United States Patent [19]

Takeda et al.

[11] Patent Number: 4,585,768
[45] Date of Patent: Apr. 29, 1986

[54] 1,5-BENZOTHIAZEPINE DERIVATIVES AND PROCESSES FOR PREPARING THE SAME

[75] Inventors: Mikio Takeda, Urawa; Tokuro Oh-ishi, Tokyo; Hiromichi Nakajima, Urawa; Taku Nagao, Tokyo, all of Japan

[73] Assignee: Tanabe Seiyaku Co., Ltd., Japan

[21] Appl. No.: 715,116

[22] Filed: Mar. 22, 1985

[30] Foreign Application Priority Data

Apr. 10, 1984 [GB] United Kingdom ............... 8409258

[51] Int. Cl.$^4$ .................. A61K 31/55; C07D 281/10
[52] U.S. Cl. ........................ 514/211; 260/239.3 B
[58] Field of Search .............. 260/239.3 B; 514/211

[56] References Cited

U.S. PATENT DOCUMENTS

| | | | |
|---|---|---|---|
| 3,075,967 | 1/1963 | Krapcho | 260/239.3 B |
| 3,341,519 | 9/1967 | Krapcho | 260/239.3 B |
| 3,562,257 | 2/1971 | Kugita et al. | 260/239.3 B |

FOREIGN PATENT DOCUMENTS

| | | | |
|---|---|---|---|
| 81234A1 | 6/1983 | European Pat. Off. | 260/239.3 B |
| 156217 | 12/1981 | Japan | 260/239.3 B |
| 156218 | 12/1981 | Japan | 260/239.3 B |

OTHER PUBLICATIONS

Murphy et al. "Proceedings National Academy of Sciences (USA)" (1983) vol. 80, No. 3, pp. 860–864.
"Circulation Research Supp. I.," Calcium Channel-- Blocking Drugs, vol. 52, pp. I-115-I-119, 1983 (Kiyomoto, et al.).

*Primary Examiner*—Robert T. Bond
*Attorney, Agent, or Firm*—Scully, Scott, Murphy & Presser

[57] ABSTRACT

Novel 1,5-benzothiazepine derivatives of the formula:

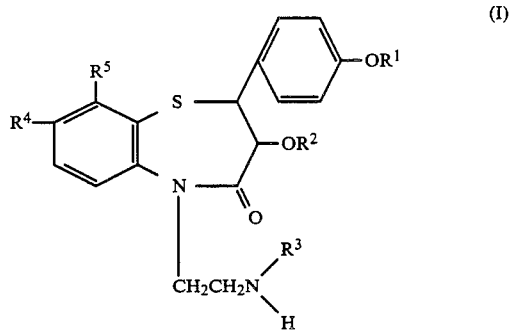

wherein $R^1$ is hydrogen or lower alkyl, $R^2$ is hydrogen, lower alkanoyl or benzyl, $R^3$ is hydrogen or lower alkyl and either one of $R^4$ and $R^5$ is hydrogen and the other is chlorine, or a pharmaceutically acceptable acid addition salt thereof are disclosed. Said derivative (I) and its salt have a potent platelet aggregation-inhibiting activity.

23 Claims, No Drawings

1,5-BENZOTHIAZEPINE DERIVATIVES AND PROCESSES FOR PREPARING THE SAME

This invention relates to novel 1,5-benzothiazepine derivatives and processes for preparing the same. More particularly, it relates to a compound of the formula:

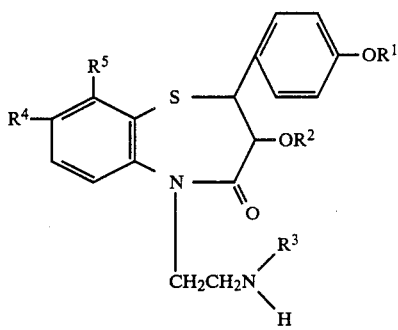

wherein $R^1$ is hydrogen or lower alkyl, $R^2$ is hydrogen, lower alkanoyl or benzyl, $R^3$ is hydrogen or lower alkyl and either one of $R^4$ and $R^5$ is hydrogen and the other is chlorine, or a pharmaceutically acceptable acid addition salt thereof.

U.S. Pat. No. 3,562,257 discloses various benzothiazepine derivatives including 7-chloro-1,5-benzothiazepine derivatives such as 2-(4-methoxyphenyl)-3-hydroxy(or acetoxy)-5-[2-(dimethylamino)ethyl]-7-chloro-2,3-dihydro-1,5-benzothiazepin-4(5H)-one. Said U.S. Patent also discloses that these benzothiazepine derivatives have antidepressive, tranquilizing and/or coronary vasodilating activity.

On the other hand, it is known that the interaction of blood constituents, especially platelets and blood coagulation factors, with blood vessel walls is causative of thrombus formation. For example, in damaged blood vessels, circulating blood platelets contact with the exposed subendothelial tissues such as collagen to release blood platelet aggregation-activating substances, and said substances cause circulating platelets to adhere to each other. The platelet aggregates thus formed at the injury site are then stabilized by fibrin, resulting in thrombus formation. Thus, the development of a platelet aggregation-inhibiting agent which suppresses the above-mentioned processes is of great importance in therapeutic treatment of thrombosis.

As a result of various investigations, we have now found that the compound (I) of the present invention or a pharmaceutically acceptable acid addition salt thereof has a potent platelet aggregation-inhibiting activity and is useful as an antithrombotic agent. The compound (I) of the present invention is especially characteristic in that, even if orally administered, said compound shows a potent and long-lasting platellet aggregation-inhibiting activity.

Representative examples of the compound of the present invention include those of the formula (I) in which $R^1$ is hydrogen or lower alkyl of one to 4 carbon atoms such as methyl, ethyl, propyl or butyl; $R^2$ is hydrogen, lower alkanoyl of 2 to 5 carbon atoms such as acetyl, propionyl, butyryl or valeryl, or benzyl; $R^3$ is hydrogen or lower alkyl of one to 4 carbon atoms such as methyl, ethyl, propyl or butyl; and either one of $R^4$ and $R^5$ is hydrogen and the other is chlorine. Among the compounds of the present invention, a preferred subgenus is those of the formula (I) in which $R^1$ is lower alkyl, $R^2$ is hydrogen or lower alkanoyl, $R^3$ is lower alkyl and either one of $R^4$ and $R^5$ is hydrogen and the other is chlorine. More preferred subgenus is those of the formula (I) in which $R^1$ is methyl, $R^2$ is hydrogen, acetyl, propionyl or butyryl, $R^3$ is methyl, ethyl or propyl and either one of $R^4$ and $R^5$ is hydrogen and the other is chlorine. Further preferred subgenus is those of the formula (I) in which $R^1$ is methyl, $R^2$ is hydrogen or acetyl, $R^3$ is methyl and either one of $R^4$ and $R^5$ is hydrogen and the other is chlorine.

While the compound (I) of the present invention can exist in the form of two diastereoisomers or four optical isomers due to the two asymmetric carbon atoms involved therein, all of these isomers or a mixture thereof are included within the scope of the invention. In the compound (I), however, the cis isomer thereof is preferred for medicinal use.

According to the present invention, the compound (I) may be prepared by either one of the methods shown in the following reaction schemes:

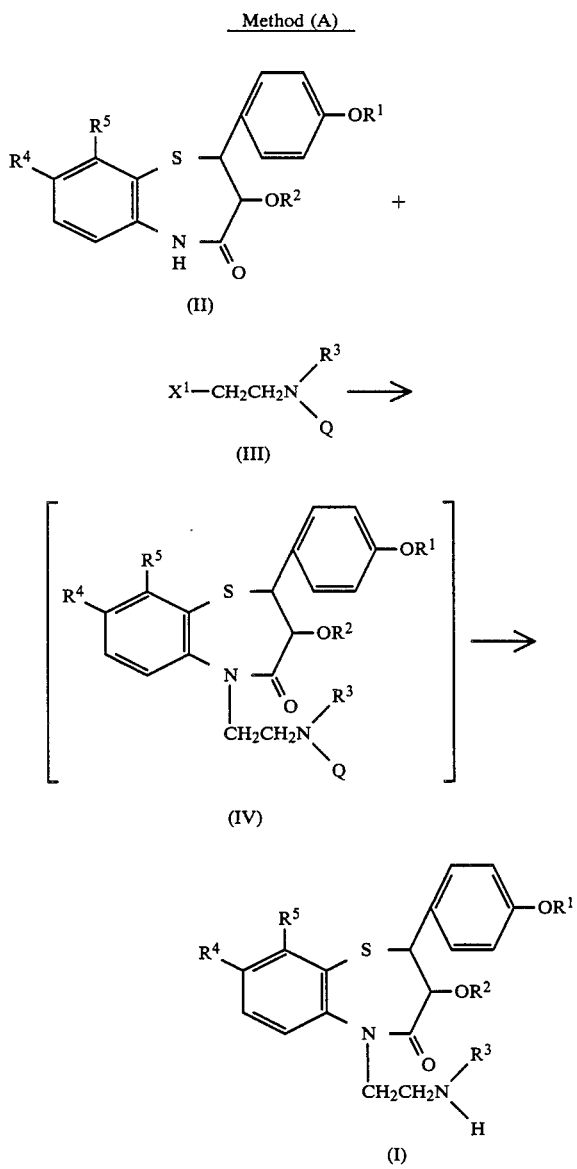

wherein Q is hydrogen or a protecting group, $X^1$ is halogen and $R^1$, $R^2$, $R^3$, $R^4$ and $R^5$ are the same as defined above.

Method (B)

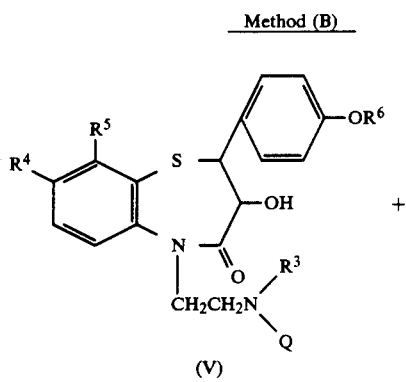

(V)

$R^7COOH$ (VI) or a reactive derivative thereof →

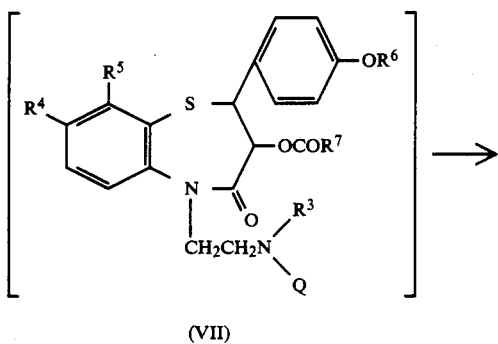

(VII)

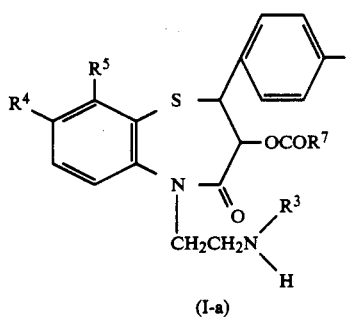

(I-a)

wherein $R^6$ and $R^7$ are lower alkyl, and $R^3$, $R^4$, $R^5$ and Q are the same as defined above.

Method (C)

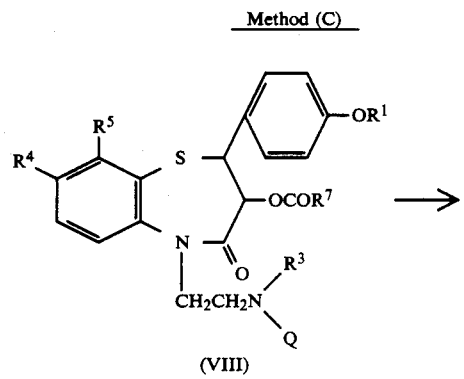

(VIII)

Method (C)
-continued

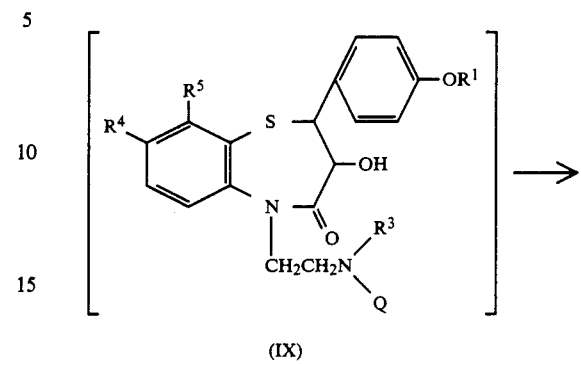

(IX)

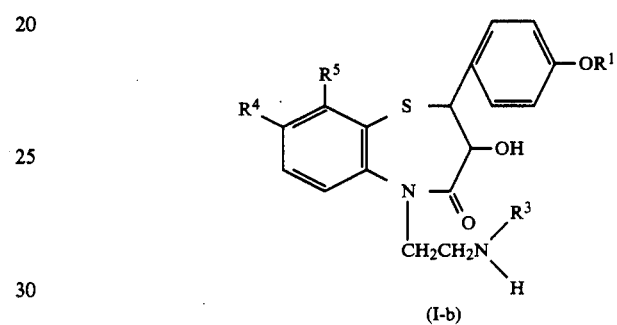

(I-b)

wherein $R^1$, $R^3$, $R^4$, $R^5$, $R^7$ and Q are the same as defined above.

Method (D)

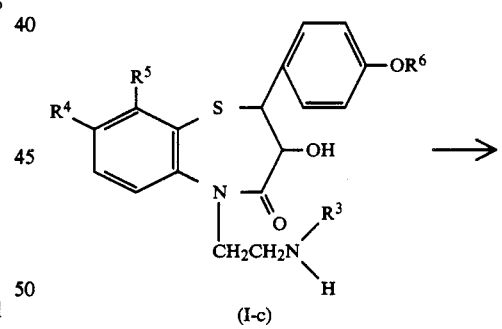

(I-c)

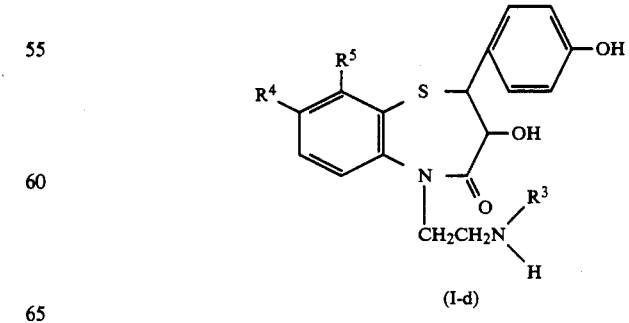

(I-d)

wherein $R^3$, $R^4$, $R^5$ and $R^6$ are the same as defined above.

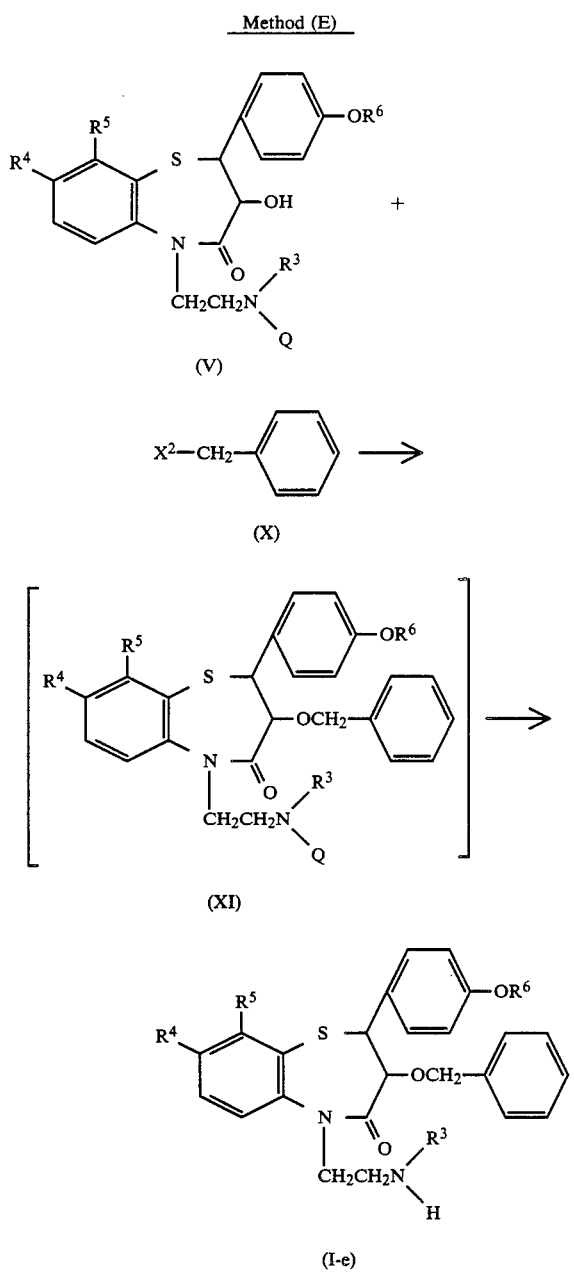

Method (E)

(V)

(X)

(XI)

(I-e)

wherein $X^2$ is halogen, and $R^3$, $R^4$, $R^5$, $R^6$ and Q are the same as defined above.

In the above-mentioned reactions, a wide variety of protecting groups which have been usually employed to protect amino groups may be used as the protecting group (Q). Examples of such protecting groups include unsubstituted or substituted benzyloxycarbonyl such as benzyloxycarbonyl or p-methoxybenzyloxycarbonyl; unsubstituted or substituted lower alkoxycarbonyl such as tert.-butoxycarbonyl, $\beta,\beta,\beta$-trichloroethoxycarbonyl or iodoethoxycarbonyl; and unsubstituted or substituted phenyl-lower alkyl such as benzyl, p-methoxybenzyl or 3,4-dimethoxybenzyl. The starting compounds (II), (V), (VIII) and (I-c) may be used either in a free form or in the form of a salt thereof. Examples of the salt of the compound (II) include alkali metal salts such as sodium salt or potassium salt. On the other hand, examples of the salt of the compounds (V), (VIII) and (I-c) include inorganic acid addition salts such as hydrochloride, hydrobromide or hydroiodide, and organic acid addition salts such as oxalate, maleate, fumarate, succinate or methanesulfonate.

According to the method (A), the compound (I) may be prepared by condensing the compound (II) or a salt thereof with the compound (III) or a salt thereof to give the compound (IV) and, when Q is a protecting group, further removing said protecting group from the compound (IV).

The condensation of the compound (II) or a salt thereof with the compound (III) or a salt thereof may be carried out in a solvent. When the compound (II) is used in a free form, it is preferred to carry out the reaction in the presence of an alkali agent. The alkali agent includes, for example, alkali metal hydroxide (e.g., potassium hydroxide, sodium hydroxide), alkali metal carbonate (e.g., potassium carbonate, sodium carbonate) and alkali metal hydride (e.g., sodium hydride). Examples of the salt of the compound (III) include acid addition salts thereof such as hydrochloride, hydrobromide and so forth. Acetone, ethyl acetate, dimethylsulfoxide, dimethylformamide and dioxane are suitable as the solvent. It is preferred to carry out the reaction at a temperature of 25° to 100° C., especially 25° to 80° C.

According to the method (B), the compound (I-a) may be prepared by condensing the compound (V) or a salt thereof with the compound (VI) or a reactive derivative thereof to give the compound (VII) and, when Q is a protecting group, further removing said protecting group from the compound (VII).

The starting compound (V) corresponds to the compound (IV) ($R^1$=lower alkyl, $R^2$=H) obtained in the first step of the method (A). Alternatively, the compound (V) in which Q is a protecting group may be prepared by introducing the protecting group into the compound (I) ($R^1$=lower alkyl, $R^2$=H). For example, the compound (V) in which Q is tert.-butoxycarbonyl may be prepared by reacting the compound (I) ($R^1$=lower alkyl, $R^2$=H) with 2-tert.-butoxycarbonylthio-4,6-dimethylpyrimidine, tert.-butoxycarbonyl chloride, tert.-butoxycarbonyl azide or tert.-butoxycarbonyl hydrazide in a solvent (e.g., dioxane, tetrahydrofuran, benzene) at a temperature of 0° to 50° C., especially 10° to 25° C.

Examples of the reactive derivative of the compound (VI) include lower alkanoic acid anhydride (e.g., acetic anhydride, propionic anhydride, butyric anhydride) and lower alkanoyl halide (e.g., acetyl chloride, propionyl chloride, butyryl chloride). The condensation of the compound (V) or a salt thereof with such reactive derivative of the compound (VI) may be carried out in a solvent in the presence or absence of an acid acceptor. The acid acceptor includes, for example, pyridine, triethylamine, N-methylpiperidine, N-methylmorpholine, N-methylpyrrolidine and N-ethyl-N,N-diisopropylamine. Pyridine, tetrahydrofuran, dioxane, benzene, toluene, methylene chloride and acetic acid are suitable as the solvent. When an excess amount of acetic anhydride is used as the reactive derivative of the compound (VI), it is not always necessary to use a solvent because said acetic anhydride serves as the solvent. It is preferred to carry out the reaction at a temperature of 20° to 130° C. if the lower alkanoic acid anhydride is used as the reactive derivative of the compound (VI); or at a temperature of 20° to 60° C. if the lower alkanoyl halide is used as the reactive derivative.

On the other hand, when the compound (VI) is used in the form of free acid, the condensation thereof with the compound (V) or a salt thereof may be carried out in the presence of a condensing agent in a solvent. The condensing agent includes, for example, dicyclohexylcarbodiimide, N,N'-carbonyldiimidazol, 1-methyl-2-halopyridinium iodide (e.g., 1-methyl-2-bromopyridinium iodide), methoxyacetylene and $(C_6H_5)_3P$-$CCl_4$. Methylene chloride, 1,2-dichloroethane, chloroform, benzene, toluene, tetrahydrofuran and dioxane are suitable as the solvent. It is preferred to carry out the reaction at a temperature of 0° to 50° C., especially 0° to 25° C.

According to the method (C), the compound (I-b) may be prepared by deacylating the compound (VIII) or a salt thereof to give the compound (IX) and, when Q is a protecting group, further removing said protecting group from the compound (IX).

Deacylation of the compound (VIII) or a salt thereof may be carried out by treating said compound with an alkali agent or an acid in a solvent. Examples of the alkali agent include alkali metal hydroxide (e.g., sodium hydroxide, potassium hydroxide) and alkali metal carbonate (e.g., sodium carbonate, potassium carbonate). On the other hand, the acid includes, for example, hydrochloric acid and hydrobromic acid. Alkanol (e.g., methanol, ethanol) and a mixture of said alkanol and water are suitable as the solvent. It is preferred to carry out the reaction at a temperature of 0° to 100° C., especially 10° to 50° C., if the alkali agent is used; or at a temperature of 0° to 100° C., especially 20° to 60° C., if the acid is used.

According to the method (D), the compound (I-d) may be prepared by dealkylating the compound (I-c) or a salt thereof. Dealkylation of the compound (I-c) or a salt thereof is conducted by treating it with boron trihalide (e.g., boron tribromide) in a solvent. Methylene chloride, chloroform, 1,2-dichloroethane and chlorobenzene are suitable as the solvent. It is preferred to carry out the reaction at a temperature of −50° to 25° C., especially −10° to 25° C.

According to the method (E), the compound (I-e) may be prepared by reacting the compound (V) or a salt thereof with a benzyl halide (X) to give the compound (XI) and, when Q is a protecting group, further removing said protecting group from the compound (XI).

The reaction of the compound (V) or a salt thereof with the compound (X) may be conducted in a solvent in the presence of an acid acceptor. The acid acceptor includes, for example, alkali metal hydride (e.g., sodium hydride) and alkali metal amide (e.g., sodium amide). Dimethylformamide, dimethylsulfoxide, benzene, tetrahydrofuran and dioxane are suitable as the solvent. It is preferred to carry out the reaction at a temperature of 0° to 80° C., especially 10° to 40° C.

Removal of the protecting group from the compound (IV), (VII), (IX) and (XI) may be conducted in a conventional manner. For example, when the protecting group is an unsubstituted or substituted benzyloxycarbonyl such as benzyloxycarbonyl or p-methoxybenzyloxycarbonyl, it is preferably removed by treating the compound (IV), (VII), (IX) or (XI) with an acid in a solvent. Hydrogen bromide or hydrogen chloride is preferably used as the acid. Acetic acid, benzene, ethyl acetate, methylene chloride, 1,2-dichloroethane, chloroform, toluene, methanol, ethanol and chlorobenzene are suitable as the solvent. It is preferred to carry out the reaction at a temperature of 0° to 40° C., especially 0° to 25° C. Tert.-butoxycarbonyl group may also be removed by treating the compound (IV), (VII), (IX) or (XI) with an acid in a solvent. Examples of the acid include hydrobromic acid, hydrochloric acid, trifluoroacetic acid and formic acid. Acetic acid and water are suitable as the solvent. It is preferred to carry out the reaction at a temperature of −10° to 50° C., especially 0° to 40° C. $\beta,\beta,\beta$-Trichloroethoxycarbonyl group may be removed by treating with zinc in acetic acid at 20° to 60° C. Further, iodoethoxycarbonyl group may be removed by treating with zinc in methanol at 20° to 60° C. When the protecting group is an unsubstituted or substituted phenyl-lower alkyl group (e.g., benzyl, p-methoxybenzyl, 3,4-dimethoxybenzyl), it may be removed by replacing it with a group which can be removed with an acid (e.g., benzyloxycarbonyl), and then removing such replaced protecting group with an acid under the same conditions as above. Replacement of the unsubstituted or substituted phenyl-lower alkyl group with the benzyloxycarbonyl group is conducted by reacting the compound (IV), (VII), (IX) or (XI) (Q=unsubstituted or substituted phenyl-lower alkyl) with benzyloxycarbonyl halide (e.g., benzyloxycarbonyl chloride) in a solvent. Benzene, toluene, xylene, dioxane and tetrahydrofuran are suitable as the solvent. It is preferred to carry out the reaction at a temperature of 50° to 130° C., especially 80° to 100° C.

Each one of the starting compounds (II), (V), (VIII) and (I-c) of the invention involves four optical isomers due to the two asymmetric carbon atoms at the 2- and 3-positions of benzothiazepine skeleton. However, since all of the above-mentioned reactions of the invention can be carried out without racemization, the compound (I) of the invention in an optically active form can be readily obtained by the use of an optically active isomer of the compound (II), (V), (VIII) or (I-c) as the starting compound.

Moreover, the starting compound (II) in which $R^2$ is hydrogen is novel and may be prepared, for example, according to the method shown in the following reaction scheme:

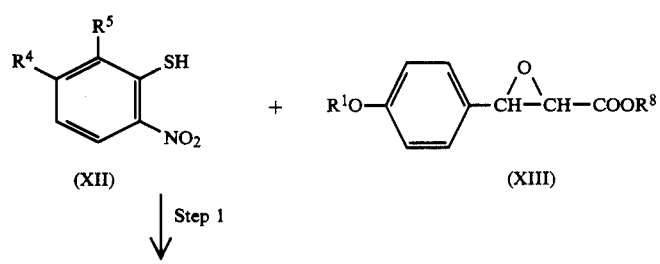

(XII)  +  (XIII)

Step 1

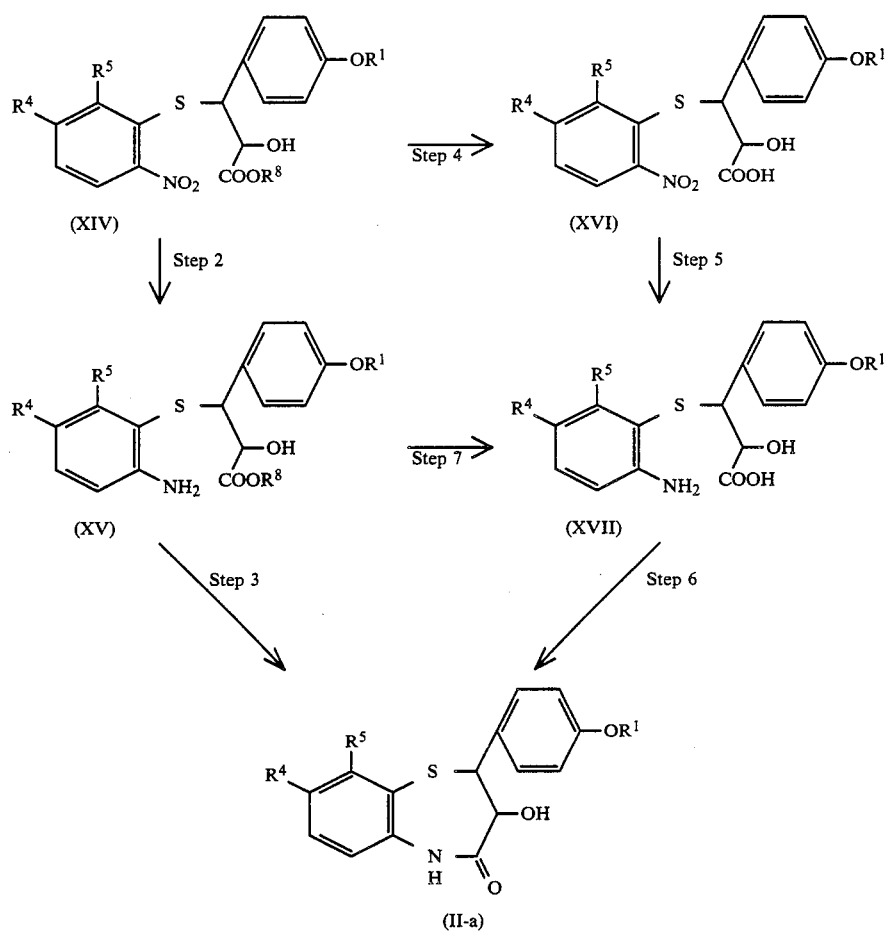

wherein $R^8$ is lower alkyl and $R^1$, $R^4$ and $R^5$ are the same as defined above.

The reaction of the compound (XII) with the compound (XIII) (i.e., Step 1) may be carried out in a solvent (e.g., toluene, xylene, benzene, acetonitrile) in the presence or absence of a Lewis acid (e.g., zinc acetate, zinc iodide, zinc chloride, stannic chloride, stannous chloride, stannic octylate, stannous stearate, boron trifluoride) at 20° to 100° C. to give the compound (XIV).

The reduction of the compound (XIV) or (XVI) (i.e., Step 2 and 5) may be carried out by subjecting it to catalytic hydrogenation in the presence of a catalyst (e.g., palladiumcharcoal, palladium black) in a solvent (e.g., water, alkanol such as methanol or ethanol, a mixture of acetic acid and said alkanol, a mixture of water and said alkanol) at 20° to 50° C. to give the compound (XV) or (XVII). It is preferred to carry out the reduction of the compound (XVI) in the presence of an alkali (e.g., sodium hydroxide or potassium hydroxide).

On the other hand, the hydrolysis of the compound (XIV) or (XV) (i.e., Step 4 and 7) may be carried out in a solvent (e.g., water, a mixture of water and alkanol such as methanol or ethanol) in the presence of an alkali agent (e.g., sodium hydroxide, potassium hydroxide, sodium carbonate, potassium carbonate) at 0° to 80° C. to give the compound (XVI) or (XVII). If required, the racemic modification of the compound (XVI) or (XVII) thus obtained may be resolved into each optical isomers thereof by the steps of reacting said compound with an optically active resolving agent (e.g., optically active isomer of lysine or p-hydroxyphenylglyicne ester) to form a pair of diastereoisomeric salts thereof, separating the diastereoisomeric salts from each other by selective crystallization, and then treating the diastereoisomeric salt with an acid (e.g., hydrochloric acid).

The intramolecular cyclization of the compound (XV) or (XVII) (i.e., Step 3 and 6) may be carried out by heating it at 110 to 160° C. either in a solvent (e.g., xylene, toluene, diphenyl ether, p-cymene and acetic acid) or without solvent. Alternatively, the intramolecular cyclization of the compound (XV) (i.e., Step 3) may be carried out at 0° to 30° C. in the presence of methylsulfinylcarbanion $(CH_3SOCH_2-)$ (prepared from dimethylsulfoxide and sodium hydride) in a solvent (e.g., dimethylsulfoxide). Moreover, the intramolecular cyclization of the compound (XVII) (i.e., Step 6) may be carried out at $-10°$ to 70° C. in a solvent (e.g., chloroform, dimethylformamide, carbon tetrachloride, dichloromethane, 1,2-dichloroethane, ethyl acetate, dioxane) in the presence of a condensing agent (e.g., dicyclohexylcarbodiimide, a mixture of dicyclohexylcarbodiimide and N-hydroxybenzotriazole).

When the compound (II-a) obtained above is a racemic modification, it may be, if required, resolved into each optical isomers thereof by using an optically active 1-(2-naphthylsulfonyl)pyrrolidine-2-carbonyl chloride as a resolving agent. For example, said optical resolution may be carried out by the steps of reacting the compound (II-a) with (S)-1-(2-naphthyl-sulfonyl)pyrrolidine-2-carbonyl chloride to give a pair of diasteroisomers, separating said diastereoisomers from each other by selective crystallization or by column chromatography, and then hydrolyzing each of diastereoisomers. Moreover, when the product obtained by hydrolysis of said diasteroisomers is a mixture of the optically active compounds (II-a) and (XVII), they can be separated from each other by taking advantage of the difference in solubilities thereof.

Alternatively, the compound (II) in which $R^1$ and $R^2$ are hydrogen may be prepared by dealkylating the compound (II-a) ($R^1$=lower alkyl) with boron trihalide (e.g., boron tribromide) under the same conditions as employed in the method (D).

On the other hand, the compound (II) in which $R^2$ is lower alkanoyl or benzyl is also novel. Among them, the compound (II) in which $R^2$ is lower alkanoyl may be prepared by acylating the compound (II-a) with a lower alkanoic acid of the formula: $R^7COOH$ (wherein $R^7$ is the same as defined above) or a reactive derivative thereof under the same conditions as employed in the first step of the method (B). In the above-mentioned reaction (i.e., acylation), the compound (II-a) in which $R^1$ is lower alkyl is preferably used as the starting compound.

The compound (I) of the invention can be used for pharmaceutical use either as the free base or as an acid addition salt thereof. Pharmaceutically acceptable acid addition salts of the compound (I) are, for example, inorganic acid addition salts such as hydrochloride, hydrobromide, hydroiodide, perchlorate, sulfate or phosphate, organic acid addition salts such as oxalate, maleate, fumarate, succinate or methanesulfonate, and so forth. These salts may be prepared, for example, by neutralizing the compound (I) with an acid. The compound (I) or a pharmaceutically acceptable acid addition salt thereof can be administered either orally or parenterally. Further, the compound (I) or its salt may be used in the form of a pharmaceutical preparation containing the same compound in conjunction or admixture with a pharmaceutical excipient suitable for oral or parenteral administration. Suitable excipients include, for example, starch, lactose, glucose, potassium phosphate, corn starch, arabic gum, stearic acid and other known medicinal excipients. The pharmaceutical preparations may be in solid form such as tablets, pills, capsules or suppositories; or in liquid form such as solutions, suspensions or emulsions. Further, when administered parenterally, the pharmaceutical preparation may be used in the form of injections.

As mentioned hereinbefore, the compound (I) of the present invention has a potent platelet aggregation-inhibiting activity and is useful for the treatment, amelioration or prophylaxis of thrombotic diseases such as cerebral infarction (or cerebral thrombosis), transient cerebral ischemia, myocardial infarction (or coronary thrombosis), pulmonary infarction, peripheral vascular embolism, thromboangitis and/or other thromboembolism (e.g., the thromboembolism following heart valve replacement).

Therapeutic dose of the compound (I) or its salt depends on route of administration, the age, weight and conditions of patients, and particular diseases to be treated. In general, however, it may be used at a dose of 0.05 to 50 mg/kg/day, especially at a dose of 0.5 to 20 mg/kg/day in the case of oral administration or at a dose of 0.05 to 10 mg/kg/day in the case of parenteral administration (e.g., intravenous injection).

Practical and presently-preferred embodiments of the present invention are illustratively shown in the following lines. Throughout the specification and claims, the terms "lower alkyl", "lower alkanoyl" and "lower alkanoic acid" should be interpreted as referring to straight or branched alkyl of one to 4 carbon atoms, straight or branched alkanoyl of 2 to 5 carbon atoms and straight or branched alkanoic acid of 2 to 5 carbon atoms, respectively. The term "threo" means that the hydroxy and phenylthio groups substituted at the 2- and 3-positions of propionic acid have threo-type configuration (i.e., said two groups are placed on opposite side of the central bond in the Fisher's projection formula).

EXPERIMENT 1

(Inhibitory Effect Ex Vivo on Collagen-Induced Platelet Aggregation of Rat Platelets)

(Method)

A test compound solution (Dose: 10 mg/kg) was orally administered to Sprague-Dawley rats fasted for about 20 hours. Three hours after administration, blood was collected from the abdominal aorta of the rats. Nine volumes of the blood were mixed with one volume of an aqueous 3.8% (w/v) trisodium citrate solution, and the mixture was centrifuged to give platelet-rich plasma ("PRP") as the supernatant solution. The bottom layer was further centrifuged to give platelet-poor plasma ("PPP") as the supernatant solution. PRP was diluted with PPP so that the blood platelet counts were $0.8-1 \times 10^6/mm^3$. 25 μl of a collagen solution (Biochim. Biophys. Acta, 186, 254(1969)) were added to 225 μl of the diluted PRP to induce platelet aggregation. The degree of platelet aggregation was examined by Born's method (Nature, 194, 927(1962)) and the percentage inhibition of platelet aggregation was calculated therefrom. The inhibitory effect of the test compound on collagen-induced platelet aggregation was estimated in terms of (−) if the percentage inhibition is less than 25%, (+) if the percentage inhibition is not less than 25% but less than 50%, and (++) if the percentage inhibition is not less than 50%.

(Results)

The results are shown in Table 1.

TABLE 1

| Compounds | Platelet aggregation-inhibiting activity |
|---|---|
| (−)-cis-2-(4-methoxyphenyl)-3-hydroxy-5-[2-(N—methylamino)-ethyl]-8-chloro-2,3-dihydro-1,5-benzothiazepin-4(5H)—one.hydrochloride | ++ |
| (−)-cis-2-(4-methoxyphenyl)-3-acetoxy-5-[2-(N—methylamino)-ethyl]-8-chloro-2,3-dihydro-1,5-benzothiazepin-4(5H)—one.oxalate | ++ |
| (+)-cis-2-(4-methoxyphenyl)-3-hydroxy-5-[2-(N—methylamino)-ethyl]-9-chloro-2,3-dihydro-1,5-benzothiazepin-4(5H)—one.hydrochloride | ++ |

EXAMPLE 1

(1) A mixture of 4.6 g of (−)-cis-2-(4-methoxyphenyl)-3-hydroxy-8-chloro-2,3-dihydro-1,5-benzothiazepin-4(5H)-one, 3.32 g of 2-(N-benzyl-N-methylamino)ethyl chloride.hydrochloride, 4.2 g of potassium carbonate and 300 ml of acetone is refluxed for 20 hours. Insoluble materials are removed by filtration, and the filtrate is evaporated under reduced pressure to remove solvent. The residue is converted to its perchlorate and then recrystallized from ethanol. 7.41 g of (−)-cis-2-(4-methoxyphenyl)-3-hydroxy-5-[2-(N-benzyl-N-methylamino)ethyl]-8-chloro-2,3-dihydro-1,5-benzothiazepin-4(5H)-one perchlorate are obtained.

M.p. 161°–163° C. (decomp.)
$[\alpha]_D^{20}$ −76 4° (C=0.589, methanol)

(2) To a refluxing solution of 4.3 g of (−)-cis-2-(4-methoxyphenyl)-3-hydroxy-5-[2-(N-benzyl-N-methylamino)ethyl]-8-chloro-2,3-dihydro-1,5-benzothiazepin-4(5H)-one in 50 ml of benzene, a solution of 4.55 g of benzyloxycarbonyl chloride in 10 ml of benzene is added dropwise for 15 minutes. The mixture is refluxed for one hour, and said mixture is evaporated under reduced pressure to remove solvent. 30 ml of ethanol and 50 ml of an aqueous sodium hydroxide solution are added to the residue, and the mixture is stirred at room temperature for 2 hours. Then, the mixture is diluted with water, and the aqueous mixture is extracted with chloroform. The extract is washed with water, dried and evaporated to remove solvent. 4.79 g of (−)-cis-2-(4-methoxyphenyl)-3-hydroxy-5-[2-(N-benzyloxycarbonyl-N-methylamino)ethyl]-8-chloro-2,3-dihydro-1,5-benzothiazepin-4(5H)-one are obtained.

The product purified by preparative thin layer chromatography shows the following physico-chemical properties.

M.p. 107.5°–108.5° C.
IR$\nu_{max}^{CHCl_3}$ (cm$^{-1}$): 3510 (OH), 1695, 1660 (C=O)
NMR (CDCl$_3$) ppm: 3.03 (3H, s, NCH$_3$), 3.80 (3H, s, OCH$_3$), 5.09 (2H, s, CH$_2$C$_6$H$_5$), 7.29 (5H, s, CH$_2$C$_6$H$_5$)
$[\alpha]_D^{20}$ −133 3° (C=0.582, methanol)

(3) 1.7 ml of 25% hydrogen bromide-acetic acid are added to a solution of 1.07 g of (−)-cis-2-(4-methoxyphenyl)-3-hydroxy-5-[2-(N-benzyloxycarbonyl-N-methylamino)ethyl]-8-chloro-2,3-dihydro-1,5-benzothiazepin-4(5H)-one in 2 ml of benzene under ice-cooling, and the mixture is stirred at room temperature for 2 hours. Then, ether is added to the mixture, and the precipitates are collected by filtration and washed with ether. Water and benzene are added to said precipitates, and the mixture is alkalized with potassium carbonate. The benzene layer is collected, washed with water, dried and then evaporated to remove solvent. Ether is added to the residue, and crystalline precipitates are collected by filtration and recrystallized from a mixture of ethyl acetate and n-hexane. 0.47 g of (−)-cis-2-(4-methoxyphenyl)-3-hydroxy-5-[2-(N-methylamino)ethyl]-8-chloro-2,3-dihydro-1,5-benzothiazepin-4(5H)-one is obtained.

M.p. 142°–145° C.
$[\alpha]_D^{20}$ −147.7° (C=0.814, chloroform)
Hydrochloride.H$_2$O:
M.p. 137°–140° C. (recrystallized from ethanol
$[\alpha]_D^{20}$ −83.9° (C=0.68, methanol)
Fumarate:
Prisms obtained by recrystallizing from methanol:
M.p. 170°–172° C. (decomp.), $[\alpha]_D^{20}$ −75.6° (C=1.00, methanol);
Needles obtained by recrystallizing from methanol:
M.p. 159-°161° C. (decomp.), $[\alpha]_D^{27}$ −74.1° (C=0.524, methanol);
Small plates obtained by recrystallizing from water:
M.p. 145°–150° C. (decomp.)
Oxalate:
M.p. 175°–177° C. (decomp.) (recrystallized from a mixture of dimethylformamide and ethanol)
Succinate.H$_2$O:
M.p. 125°–128° C. (decomp.) (recrystallized from ethanol)
Hydrobromide.H$_2$O:
M.p. 137°–138° C. (decomp.) (recrystallized from ethanol)
Sulfate:
M.p. 105°–128° C. (recrystallized from a mixture of ethanol and water)

EXAMPLE 2

(1) (−)-cis-2-(4-Methoxyphenyl)-3-hydroxy-5-[2-(N-benzyl-N-methylamino)ethyl]-8-chloro-2,3-dihydro-1,5-benzothiazepin-4(5H)-one obtained from 6 g of its perchlorate is dissolved in 93 ml of benzene, and the solution is refluxed. To said refluxing solution, a solution of 5.28 g of benzyloxycarbonyl chloride in 12 ml of benzene is added dropwise, and the mixture is refluxed for 4 hours. The mixture is evaporated under reduced pressure to remove solvent. 5.42 g of (−)-cis-2-(4-methoxyphenyl)-3-hydroxy-5-[2-(N-benzyloxycarbonyl-N-methylamino)ethyl]-8-chloro-2,3-dihydro-1,5-benzothiazepin-4(5H)-one are obtained.

The physico-chemical properties of this product are identical with those of the product obtained in Example 1-(2).

(2) 2.71 g of (−)-cis-2-(4-methoxyphenyl)-3-hydroxy-5-[2-(N-benzyloxycarbonyl-N-methylamino)ethyl]-8-chloro-2,3-dihydro-1,5-benzothiazepin-4(5H)-one are dissolved in 30 ml of ethanol, and the solution is saturated with gaseous hydrogen chloride under ice-cooling. The saturated solution is stirred at room temperature for 20 hours. The solution is evaporated under reduced pressure at a temperature below 35° C. to remove solvent. The residue is dissolved in benzene, and the solution is extracted with conc. HCl-H$_2$O. The aqueous layer is collected, washed with benzene, alkalized with potassium carbonate and then extracted with chloroform. The extract is washed with water, dried and then evaporated to remove solvent. Isopropyl ether is added to the residue, and crystalline precipitates are collected by filtration. 1.83 g of (−)-cis-2-(4-methoxyphenyl)-3-hydroxy-5-[2-(N-methylamino)ethyl]-8-chloro-2,3-dihydro-1,5-benzothiazepin-4(5H)-one are obtained.

The physico-chemical properties of this product are identical with those of the product obtained in Example 1-(3).

EXAMPLE 3

A mixture of 1.4 g of (−)-cis-2-(4-methoxyphenyl)-3-hydroxy-8-chloro-2,3-dihydro-1,5-benzothiazepin-4(5H)-one, 0.54 g of potassium hydroxide and 14 ml of dimethylsulfoxide is stirred at room temperature for one hour. Then, 0.56 g of 2-aminoethyl chloride.hydrochloride is added to the mixture, and said mixture is stirred at room temperature for 25 hours. The mixture is poured into ice-water, and the precipitated crystals are collected by filtration. The crystals are treated with a mixture of 10% hydrochloric acid and chloroform, and insoluble materials are removed by filtration. The filtrate is alkalized with ammonia, and the chloroform layer is collected therefrom. The aqueous layer is extracted with chloroform, and the extracts are combined with the chloroform layer obtained above. The combined solution is washed with water, dried and evaporated to remove solvent. The residue (oil, 0.47 g) is purified by silica gel chromatography (Solvent: chloroform-methanol (20:1)), converted to its hydrochloride, and then recrystallized from aqueous ethanol. 0.14 g of (—)-cis-2-(4-methoxyphenyl)-3-hydroxy-5-(2-aminoethyl)-8-chloro-2,3-dihydro-1,5-benzothiazepin-4(5H)-one.hydrochloride.½H$_2$O is obtained.

M.p. 155°–158° C. (decomp.)
$[\alpha]_D^{20}$ −88.0° (C=0.5, methanol)

EXAMPLE 4

(1) A mixture of 3.0 g of (—)-cis-2-(4-methoxyphenyl)-3-acetoxy-8-chloro-2,3-dihydro-1,5-benzothiazepin-4(5H)-one, 1.9 g of 2-(N-benzyl-N-methylamino)ethyl chloride.hydrochloride, 3.3 g of potassium carbonate and 80 ml of acetone is refluxed for 20 hours. Insoluble materials are removed by filtration, and the filtrate is evaporated under reduced pressure to remove solvent. The residue is dissolved in ethyl acetate, and the solution is washed with water, dried and evaporated to remove solvent. 2.9 g of (—)-cis-2-(4-methoxyphenyl)-3-acetoxy-5-[2-(N-benzyl-N-methylamino)ethyl]-8-chloro-2,3-dihydro-1,5-benzothiazepin-4(5H)-one are obtained as an oil.

Oxalate:
M.p. 192°–194° C. (decomp.) (recrystallized from ethanol)
$[\alpha]_D^{20}$ −96.5° (C=1.0, dimethylformamide)

(2) A solution of 27.5 g of (—)-cis-2-(4-methoxyphenyl)-3-acetoxy-5-[2-(N-benzyl-N-methylamino)ethyl]-8-chloro-2,3-dihydro-1,5-benzothiazepin-4(5H)-one in 600 ml of benzene is refluxed, and a solution of 26.2 g of benzyloxycarbonyl chloride in 80 ml of benzene is added dropwise thereto during 10 minutes. The mixture is refluxed for 6 hours. Then the mixture is evaporated under reduced pressure to remove solvent. The residue is washed with n-hexane, whereby 37.5 g of (—)-cis-2-(4-methoxyphenyl)-3-acetoxy-5-[2-(N-benzyloxycarbonyl-N-methylamino)ethyl]-8-chloro-2,3-dihydro-1,5-benzothiazepin-4(5H)-one are obtained as an oil.

The product purified by preparative thin layer chromatography shows the following physico-chemical properties.

IR$\nu_{max}^{CHCl_3}$ (cm$^{-1}$): 1740, 1685
NMR (CDCl$_3$) ppm: 1.90 (3H, s, OCOC$\underline{H}_3$), 3.03 (3H, s, NC$\underline{H}_3$), 3.81 (3H, s, OC$\underline{H}_3$), 5.08 (2H, s, C$\underline{H}_2$C$_6$H$_5$), 7.32 (5H, s, C$_6$$\underline{H}_5$)
$[\alpha]_D^{20}$ −115.4° (C=1.0, methanol)

(3) 37.5 g of (—)-cis-2-(4-methoxyphenyl)-3-acetoxy-5-[2-(N-benzyloxycarbonyl-N-methylamino)ethyl]-8-chloro-2,3-dihydro-1,5-benzothiazepin-4(5H)-one, 75 ml of 25% hydrogen bromide-acetic acid and 95 ml of methylene chloride are mixed under ice-cooling, and the mixture is stirred at room temperature for 3 hours. Then, the mixture is evaporated under reduced pressure to remove methylene chloride. Ether is added to the residue, and the ether layer is removed by decantation. The precipitates are washed with ether and dissolved in water. The solution is neutrallized with potassium carbonate and extracted with ethyl acetate. The extract is washed with water, dried and evaporated to remove solvent. The residue is converted to its oxalate and recrystallized from methanol. 18.7 g of (—)-cis-2-(4-methoxyphenyl)-3-acetoxy-5-[2-(N-methylamino)ethyl]-8-chloro-2,3-dihydro-1,5-benzothiazepin-4(5H)-one.oxalate are obtained.

M.p. 175°–177° C. (decomp.)

$[\alpha]_D^{20}$ −74.2° (C=0.814, methanol)

EXAMPLE 5

(1) A mixture of 9 g of (±)-cis-2-(4-methoxyphenyl)-3-hydroxy-8-chloro-2,3-dihydro-1,5-benzothiazepin-4(5H)-one, 7.7 g of 2-(N-benzyl-N-methylamino)ethyl chloride hydrochloride, 9.62 g of potassium carbonate and 600 ml of acetone is treated in the same manner as described in Example 4-(1). 14.8 g of (±)-cis-2-(4-methoxyphenyl)-3-hydroxy-5-[2-(N-benzyl-N-methylamino)ethyl]-8-chloro-2,3-dihydro-1,5-benzothiazepin-4(5H)-one are obtained as an oil.

(2) A solution of 13.5 g of (±)-cis-2-(4-methoxyphenyl)-3-hydroxy-5-[2-(N-benzyl-N-methylamino)ethyl]-8-chloro-2,3-dihydro-1,5-benzothiazepin-4(5H)-one in 200 ml of benzene is refluxed under heating, and a solution of 14.3 g of benzyloxycarbonyl chloride in 30 ml of benzene is added dropwise thereto for 30 minutes. The mixture is refluxed for one hour. Then, the mixture is evaporated under reduced pressure to remove solvent. The residue is washed with n-hexane, whereby 15.4 g of (±)-cis-2-(4-methoxyphenyl)-3-hydroxy-5-[2-(N-benzyloxycarbonyl-N-methylamino)ethyl]-8-chloro-2,3-dihydro-1,5-benzothiazepin-4(5H)-one are obtained as an oil.

IR$\nu_{max}^{CHCl_3}$ (cm$^{-1}$): 3510, 1695, 1660
NMR (CDCl$_3$) ppm: 3.03 (3H, s, NC$\underline{H}_3$), 3.80 (3H, s, OC$\underline{H}_3$), 5.09 (2H, s, C$\underline{H}_2$C$_6$H$_5$), 7.29 (5$\underline{H}$, s, C$_6$H$_5$)

(3) A mixture of 2.9 g of (±)-cis-2-(4-methoxyphenyl)-3-3-hydroxy-5-[2-(N-benzyloxycarbonyl-N-methylamino)ethyl]-8-chloro-2,3-dihydro-1,5-benzothiazepin-4(5H)-one, 25 ml of acetic anhydride and 2 ml of pyridine is stirred at 110° C. for 3 hours. Then, the mixture is evaporated to remove solvent. Benzene is added to the residue, and the mixture is evaporated under reduced pressure to remove solvent. 3.1 g of (±)-cis-2-(4-methoxyphenyl)-3-acetoxy-5-[2-(N-benzyloxycarbonyl-N-methylamino)ethyl]-8-chloro-2,3-dihydro-1,5-benzothiazepin-4(5H)-one are obtained as an oil.

IR$\nu_{max}^{CHCl_3}$ (cm$^{-1}$): 1740, 1685
NMR (CDCl$_3$) ppm: 1.90 (3H, s, OCOC$\underline{H}_3$), 3.03 (3H, s, NC$\underline{H}_3$), 3.81 (3H, s, OC$\underline{H}_3$), 5.08 (2H, s, C$\underline{H}_2$C$_6$H$_5$), 7.32 (5H, s, C$_6$H$_5$)

(4) A mixture of 3.1 g of (±)-cis-2-(4-methoxyphenyl)-3-acetoxy-5-[2-(N-benzyloxycarbonyl-N-methylamino)ethyl]-8-chloro-2,3-dihydro-1,5-benzothiazepin-4(5H)-one, 5 ml of 25% hydrogen bromide-acetic acid and 10 ml of acetic acid is stirred at room temperature for 2 hours. Then, ether is added to the mixture. The crystalline precipitates are collected by filtration and recrystallized from a mixture of ethanol and ether. 1.51 g of (±)-cis-2-(4-methoxyphenyl)-3-acetoxy-5-[2-(N-methylamino)ethyl]-8-chloro-2,3-dihydro-1,5-benzothiazepin-4(5H)-one hydrobromide.C$_2$H$_5$OH½H$_2$O are obtained.

M.p. 129°–131° C. (decomp.)

EXAMPLE 6

(1) A solution of 5.37 g of 2-(N-benzyloxycarbonyl-N-methylamino)ethyl chloride in 20 ml of dimethylformamide is added dropwise at 50° C. to a mixture of 6.1 g of (±)-cis-2-(4-methoxyphenyl)-3-hydroxy-8-chloro-2,3-dihydro-1,5-benzothiazepin-4(5H)-one, 1.23 g of potassium hydroxide and 40 ml of dimethylformamide. The mixture is stirred at 50° C. for 5 days. Then, the mixture is poured into ice-water, and the aqueous mixture is extracted with ethyl acetate. The extract is washed with water, dried and evaporated to remove solvent. Ethyl acetate is added to the residue, and insoluble materials are removed by filtration. The filtrate is evaporated to remove solvent, and the residue is purified by silica gel chromatography (Solvent: chloroform-ethyl acetate (10:1)), whereby 2.9 g of (±)-cis-2-(4-methoxyphenyl)-3-hydroxy-5-[2-(N-benzyloxycarbonyl-N-methylamino)ethyl]-8-chloro-2,3-dihydro-1,5-benzothiazepin-4(5H)-one are obtained as an oil.

The physico-chemical properties of this product are identical with those of the product obtained in Example 5-(2).

(2) The product obtained in paragraph (1) is treated in the same manner as described in Example 5-(3) and (4), whereby (±)-cis-2-(4-methoxyphenyl)-3-acetoxy-5-[2-(N-methylamino)ethyl]-8-chloro-2,3-dihydro-1,5-benzothiazepin-4(5H)-one.hydrobromide.$C_2H_5OH.\frac{1}{2}H_2O$ is obtained.

The pysico-chemical properties of this product are identical with those of the product obtained in Example 5-(4).

EXAMPLE 7

(1) A mixture of 6.22 g of (−)-cis-2-(4-methoxyphenyl)-3-hydroxy-5-[2-(N-benzyl-N-methylamino)ethyl]-8-chloro-2,3-dihydro-1,5-benzothiazepin-4(5H)-one, 60 ml of acetic anhydride and one ml of pyridine is refluxed for 4 hours. Then, the mixture is evaporated under reduced pressure to remove solvent. Benzene is added to the residue, and the mixture is evaporated under reduced pressure. 7 g of (−)-cis-2-(4-methoxyphenyl)-3-acetoxy-5-[2-(N-benzyl-N-methylamino)ethyl]-8-chloro-2,3-dihydro-1,5-benzothiazepin-4(5H)-one are obtained as an oil.

The physico-chemical properties of this product are identical with those of the product obtained in Example 4-(1).

(2) 27.5 g of (−)-cis-2-(4-methoxyphenyl)-3-acetoxy-5-[2-(N-benzyl-N-methylamino)ethyl]-8-chloro-2,3-dihydro-1,5-benzothiazepin-4(5H)-one obtained in paragraph (1) is treated in the same manner as described in Example 4-(2) and (3), whereby 18.7 g of (−)-cis-2-(4-methoxyphenyl)-3-acetoxy-5-[2-(N-methylamino)ethyl]-8-chloro-2,3-dihydro-1,5-benzothiazepin-4(5H)-one.oxalate are obtained.

The physico-chemical properties of this product are identical with those of the product obtained in Example 4-(3).

EXAMPLE 8

(1) A mixture of one g of (+)-cis-2-(4-methoxyphenyl)-3-hydroxy-8-chloro-2,3-dihydro-1,5-benzothiazepin-4(5H)-one, 0.72 g of 2-(N-benzyl-N-methylamino)ethyl chloride.hydrochloride, 1.2 g of potassium carbonate and 15 ml of acetone is treated in the same manner as described in Example 1-(1). The crude product is converted to its perchlorate and recrystallized from ethanol. 1.61 g of (+)-cis-2-(4-methoxyphenyl)-3-hydroxy-5-[2-(N-benzyl-N-methylamino)ethyl]-8-chloro-2,3-dihydro-1,5-benzothiazepin-4(5H)-one.perchlorate are obtained.

M.p. 161°–163° C. (decomp.)
$[\alpha]_D^{20}$ +76.5° (C=0.446, methanol)

(2) A mixture of 1.35 g of (+)-cis-2-(4-methoxyphenyl)-3-hydroxy-5-[2-(N-benzyl-N-methylamino)ethyl]-8-chloro-2,3-dihydro-1,5-benzothiazepin-4(5H)-one, 12 ml of acetic anhydride and 6 drops of pyridine is treated in the same manner as described in Example 7-(1), whereby 1.52 g of (+)-cis-2-(4-methoxyphenyl)-3-acetoxy-5-[2-(N-benzyl-N-methylamino)ethyl]-8-chloro-2,3-dihydro-1,5-benzothiazepin-4(5H)-one are obtained as an oil.

Oxalate:
M.p. 191°–194° C. (decomp.) (recrystallized from ethanol)
$[\alpha]_D^{20}$ +96.8° (C=0.73, dimethylformamide)

(3) 1.52 g of (+)-cis-2-(4-methoxyphenyl)-3-acetoxy-5-[2-(N-benzyl-N-methylamino)ethyl]-8-chloro-2,3-dihydro-1,5-benzothiazepin-4(5H)-one, 1.24 g of benzyloxycarbonyl chloride and 18 ml of benzene are treated in the same manner as described in Example 4-(2), whereby 1.64 g of (+)-cis-2-(4-methoxyphenyl)-3-acetoxy-5-[2-(N-benzyloxycarbonyl-N-methylamino)ethyl]-8-chloro-2,3-dihydro-1,5-benzothiazepin-4(5H)-one are obtained as an oil.

(4) A mixture of 1.64 g of (+)-cis-2-(4-methoxyphenyl)-3-acetoxy-5-[2-(N-benzyloxycarbonyl-N-methylamino)ethyl]-8-chloro-2,3-dihydro-1,5-benzothiazepin-4(5H)-one, 4.5 ml of 25% of hydrogen bromide-acetic acid and 18 ml of acetic acid are treated in the same manner as described in Example 4-(3). The crude product thus obtained is converted to its oxalate and recrystallized from methanol. 1.04 g of (+)-cis-2-(4-methoxyphenyl)-3-acetoxy-5-[2-(N-methylamino)ethyl]-8-chloro-2,3-dihydro-1,5-benzothiazepin-4(5H)-one.oxalate.$H_2O$ are obtained.

M.p. 172°–173° C. (decomp.)
$[\alpha]_D^{20}$ +63.3° (C=0.422, methanol)

EXAMPLE 9

(1) A mixture of 1.02 g of (±)-cis-2-(4-methoxyphenyl)-3-hydroxy-5-[2-(N-benzyl-N-methylamino)ethyl]-8-chloro-2,3-dihydro-1,5-benzothiazepin-4(5H)-one, 10 ml of acetic anhydride and one ml of pyridine is stirred at 100° C. for 3 hours. Then, the mixture is evaporated under reduced pressure. Benzene is added to the mixture, and the mixture is evaporated to remove solvent. 0.65 g of (±)-cis-2-(4-methoxyphenyl)-3-acetoxy-5-[2-(N-benzyl-N-methylamino)ethyl]-8-chloro-2,3-dihydro-1,5-benzothiazepin-4(5H)-one is obtained.

M.p. 106°–110° C. (decomp.)
Hydrochloride.$H_2O$:
M.p. 228°–231° C. (recrystallized from a mixture of chloroform, ethanol and ether)

(2) The product of obtained in paragraph (1) is treated in the same manner as described in Example 4-(2) and (3), whereby (±)-cis-2-(4-methoxyphenyl)-3-acetoxy-5-[2-(N-methylamino)ethyl]-8-chloro-2,3-dihydro-1,5-benzothiazepin-4(5H)-one is obtained.

Hydrobromide.$C_2H_5OH.\frac{1}{2}H_2O$:
The physico-chemical properties of this product are identical with those of the product obtained in Example 5-(4).

EXAMPLE 10

(1) A mixture of 3.36 g of (−)-cis-2-(4-methoxyphenyl)-3-hydroxy-8-chloro-2,3-dihydro-1,5-benzothiazepin-4(5H)-one, 2.58 g of 2-(N-benzyl-N-ethylamino)ethyl chloride.hydrochloride, 4.15 g of potassium carbonate, 100 ml of acetone and one ml of water is treated in the same manner as described in Example 1-(1). The crude product thus obtained is converted to its fumarate and recrystallized from a mixture of ethanol and ether. 4.33 g of (−)-cis-2-(4-methoxyphenyl)-3-hydroxy-5-[2-(N-benzyl-N-ethylamino)e- thyl]-8-chloro-2,3-dihydro-1,5-benzothiazepin-4(5H)-one.½ fumarate are obtained.

M.p. 119°–122° C.

$[\alpha]_D^{20}$ −104.2° (C=1.0, methanol)

(2) A mixture of 3.82 g of (−)-cis-2-(4-methoxyphenyl)-3-hydroxy-5-[2-(N-benzyl-N-ethylamino)ethyl]-8-chloro-2,3-dihydro-1,5-benzothiazepin-4(5H)-one, 38 ml of acetic anhydride and 10 drops of pyridine is treated in the same manner as described in Example 7-(1). The crude product thus obtained is converted to its oxalate and recrystallized from a mixture of ethanol and ether. 4.4 g of (−)-cis-2-(4-methoxyphenyl)-3-acetoxy-5-[2-(N-benzyl-N-ethylamino)ethyl]-8-chloro-2,3-dihydro-1,5-benzothiazepin-4(5H)-one.oxalate.½ C$_2$H$_5$OH are obtained.

M.p. 140°–147° C.

$[\alpha]_D^{20}$ −77.6° (C=0.60, methanol)

(3) 3.7 g of (−)-cis-2-(4-methoxyphenyl)-3-acetoxy-5-[2-(N-benzyl-N-ethylamino)ethyl]-8-chloro-2,3-dihydro-1,5-benzothiazepin-4(5H)-one, 2.78 g of benzyloxycarbonyl chloride and 44 ml of benzene are treated in the same manner as described in Example 5-(2), whereby 4.24 g of (−)-cis-2-(4-methoxyhenyl)-3-acetoxy-5-[2-(N-benzyloxycarbonyl-N-ethylamino)ethyl]-8-chloro-2,3-dihydro-1,5-benzothiazepin-4(5H)-one are obtained as an oil.

IR$\nu_{max}^{liq}$(cm$^{-1}$): 1745, 1690

NMR (CDCl$_3$) ppm: 1.15 (3H, t, CH$_2$C$\underline{H}_3$), 1.90 (3H, s, COC$\underline{H}_3$), 3.82 (3H, s, OC$\underline{H}_3$), 5.09 (2H, s, C$\underline{H}_2$C$_6$H$_5$)

(4) A mixture of 4.13 g of (−)-cis-2-(4-methoxyphenyl)-3-acetoxy-5-[2-(N-benzyloxycarbonyl-N-ethylamino)ethyl]-1-8-chloro-2,3-dihydro-1,5-benzothiazepin-4(5H)-one, 12.5 ml of 25% hydrogen bromide-acetic acid and 45 ml of acetic acid is treated in the same manner as described in Example 4-(3). The crude product thus obtained is converted to its oxalate and resrystallized from methanol. 2.53 g of (−)-cis-2-(4-methoxyphenyl)-3-acetoxy-5-[2-(N-ethylamino)ethyl]-8-chloro-2,3-dihydro-1,5-benzothiazepin-4(5H)-one.oxalate are obtained.

M.p. 172°–173.5° C. (decomp.)

$[\alpha]_D^{20}$ −79.2° (C=1.0, methanol)

EXAMPLE 11

(1) A mixture of 3.36 g of (−)-cis-2-(4-methoxyphenyl)-3-hydroxy-8-chloro-2,3-dihydro-1,5-benzothiazepin-4(5H)-one, 2.73 g of 2-(N-benzyl-N-n-propylamino)ethyl chloride.hydrochloride, 4.15 g of potassium carbonate, 100 ml of acetone and one ml of water is treated in the same manner as described in Example 1-(1). The crude product thus obtained is purified by silica gel chromatography (Solvent: chloroform), whereby 5.06 g of (−)-cis-2-(4-methoxyphenyl)-3-hydroxy-5-[2-(N-benzyl-N-n-propylamino)ethyl]-8-chloro-2,3-dihydro-1,5-benzothiazepin-4(5H)-one are obtained as an oil.

$[\alpha]_D^{20}$ −119.4° (C=1.0, methanol)

IR$\nu_{max}^{liq}$ (cm$^{-1}$): 3480 (OH), 1660 (C=O)

NMR (CDCl$_3$) ppm: 0.87 (3H, t, J=7 Hz, CH$_2$C$\underline{H}_3$), 3.61 (2H, s, C$\underline{H}_2$C$_6$H$_5$), 3.80 (3H, s, OC$\underline{H}_3$), 7.21 (5$\underline{H}$, s, C$_6$H$_5$)

(2) A mixture of 5.06 g of (−)-cis-2-(4-methoxyphenyl)-3-hydroxy-5-[2-(N-benzyl-N-n-propylamino)ethyl]-8-chloro-2,3-dihydro-1,5-benzothiazepin-4(5H)-one, 51 ml of acetic anhydride and 10 drops of pyridine is treated in the same manner as described in Example 7-(1). The crude product thus obtained is converted to its oxalate and recrystallized from isopropanol. 5.58 g of (−)-cis-2-(4-methoxyphenyl)-3-acetoxy-5-[2-(N-benzyl-N-n-propylamino)ethyl]-8-chloro-2,3-dihydro-1,5-benzothiazepin-4(5H)-one.oxalate are obtained.

M.p. 159°–160° C.(decomp.)

$[\alpha]_D^{20}$ −84.6° (C=1.0, methanol)

(3) 4.79 g of (−)-cis-2-(4-methoxyphenyl)-3-acetoxy-5-[2-(N-benzyl-N-n-propylamino)ethyl]-8-chloro-2,3-dihydro-1,5-benzothiazepin-4(5H)-one, 3.41 g of benzyloxycarbonyl chloride and 57 ml of benzene are treated in the same manner as described in Example 5-(2), whereby 4.95 g of (−)-cis-2-(4-methoxyphenyl)-3-acetoxy-5-[2-(N-benzyloxycarbonyl-N-n-propylamino)ethyl]-8-chloro-2,3-dihydro-1,5-benzothiazepin-4(5H)-one are obtained as an oil.

IR$\nu_{max}^{liq}$ (cm$^{-1}$): 1745, 1685

NMR (CDCl$_3$) ppm: 0.90 (3H, t, CH$_2$C$\underline{H}_3$), 1.90 (3H, s, COC$\underline{H}_3$), 3.83 (3H, s, OC$\underline{H}_3$), 5.09 (2$\underline{H}$, s, C$\underline{H}_2$C$_6$H$_5$)

(4) A mixture of 4.9 g of (−)-cis-2-(4-methoxyphenyl)-3-acetoxy-5-[2-(N-benzyloxycarbonyl-N-n-propylamino)ethy]-8-chloro-2,3-dihydro-1,5-benzothiazepin-4(5H)-one, 14.5 ml of 25% hydrogen bromide-acetic acid and 50 ml of acetic acid is treated in the same manner as described in Example 4-(3). The crude product thus obtained is converted to its fumarate and recrystallized from a mixture of ethanol and ether. 3.44 g of (−)-cis-2-(4-methoxyphenyl)-3-acetoxy-5-[2-(N-n-propylamino)ethyl]-8-chloro-2,3-dihydro-1,5-benzothiazepin-4(5H)-one.fumarate.½ H$_2$O are obtained.

M.p. 128°–131° C. (decomp.)

$[\alpha]_D^{20}$ −77.8° (C=1.0, methanol)

EXAMPLE 12

(1) 490 mg of propionyl chloride are added under ice-cooling to a solution of 2.15 g of (−)-cis-2-(4-methoxyphenyl)-3-hydroxy-5-[2-(N-benzyloxycarbonyl-N-methylamino)ethyl]-8-chloro-2,3-dihydro-1,5-benzothiazepin-4(5H)-one in 20 ml of pyridine, and the mixture is stirred at room temperature for 3 hours. Then, the mixture is evaporated under reduced pressure. The residue is several times evaporated together with benzene, and ice-water is added to said residue. The aqueous mixture is extracted with ethyl acetate, and the extract is washed with water, 10% hydrochloric acid, water, an aqueous saturated sodium bicarbonate solution and water, successively. Said extract is dried and evaporated under reduced pressure to remove solvent. 2.19 g of (−)-cis-2-(4-methoxyphenyl)-3-propionyloxy-5-[2-(N-benzyloxycarbonyl-N-methylamino)ethyl]-8-chloro-2,3-dihydro-1,5-benzothiazepin-4(5H)-one are obtained as caramel.

(2) A mixture of 985 mg of (−)-cis-2-(4-methoxyphenyl)-3-propionyloxy-5-[2-(N-benzyloxycarbonyl-N-methylamino)ethyl]-8-chloro-2,3-dihydro-1,5-benzothiazepin-4(5H)-one, 1.6 ml of 25% hydrogen bromide-acetic acid and 5 ml of benzene is stirred for 5 hours under ice-cooling. Then, the mixture is evaporated at room temperature to remove benzene. Ether is added to the residue, and the precipitates are collected by filtration and washed with ether. Water is added to said precipitates, and the aqueous mixture is neutralized with potassium carbonate and extracted with ethyl acetate. The extract is washed with water, dried and evaporated under reduced pressure to remove solvent. 660 mg of (−)-cis-2-(4-methoxyphenyl)-3-propionyloxy-5-[2-(N-methylamino)ethyl]-8-chloro-2,3-dihydro-1,5-benzothiazepin-4(5H)-one are obtained as caramel.

IR$\nu_{max}^{CHCl_3}$ (cm$^{-1}$): 1740, 1675
Mass (m/e):449 (M+)
NMR (CDCl$_3$) ppm: 0.95 (3H, t, J=7.5, COCH$_2$CH$_3$), 2.42 (3H, s, NHCH$_3$), 3.81 (3H, s, OCH$_3$), 5.11 (2H, q, COCH$_2$CH$_3$, J=7.5)
$[\alpha]_D^{20}$ −74.3° (C=1.01, chloroform)

EXAMPLE 13

(1) 2.06 g of (−)-cis-2-(4-methoxyphenyl)-3-hydroxy-5-[2-(N-benzyloxycarbonyl-N-methylamino)ethyl]-8-chloro-2,3-dihydro-1,5-benzothiazepin-4(5H)-one 460 mg of n-butyryl chloride and 20 ml of pyridine are treated in the same manner as described in Example 12-(1), whereby 2.3 g of (−)-cis-2-(4-methoxyphenyl)-3-n-butyryloxy-5-[2-(N-benzyloxycarbonyl-N-methylamino)ethyl]-8-chloro-2,3-dihydro-1,5-benzothiazepin-4(5H)-one are obtained as caramel.

(2) A mixture of 2.20 g of (−)-cis-2-(4-methoxyphenyl)-3-n-butyryloxy-5-[2-(N-benzyloxycarbonyl-N-methylamino)ethyl]-8-chloro-2,3-dihydro-1,5-benzothiazepin-4(5H)-one, 5 ml of 25% hydrogen bromide-acetic acid and 20 ml of acetic acid is stirred at room temperature for 4 hours. Then, ice-water is added to the mixture, and the aqueous mixture is washed with ether. The aqueous layer is neutralized with potassium carbonate and extracted with ethyl acetate. The extract is washed with water, dried and evaporated under reduced pressure to remove solvent. The residue (1.48 g, brown caramel) is purified by silica gel chromatography (Solvent: chloroformethanol (10:1)), whereby 0.73 g of (−)-cis-2-(4-methoxyphenyl)-3-n-butyryloxy-5-[2-(N-methylamino)ethyl]-8-chloro-2,3-dihydro-1,5-benzothiazepin-4(5H)-one is obtained as caramel.

IR $\nu_{max}^{CHCl_3}$ (cm$^{-1}$): 1735, 1680
NMR (CDCl$_3$) ppm: 0.82 (3H, t, CH$_2$CH$_3$), 2.47 (3H, s, NHCH$_3$), 3.82 (3H, s, OCH$_3$)
$[\alpha]_D^{20}$ −71.2° (C=0.98, chloroform)

EXAMPLE 14

A mixture of 0.09 g of (−)-cis-2-(4-methoxyphenyl)-3-hydroxy-5-(2-aminoethyl)-8-chloro-2,3-dihydro-1,5-benzothiazepin-4(5H)-one.hydrochloride, one ml of acetyl chloride and 10 ml of methylene chloride is stirred at room temperature for 24 hours. Then, the mixture is evaporated under reduced pressure to remove solvent. Ether is added to the residue, and the precipitated crystals are collected by filtration. The crystals are dissolved in water, and the aqueous solution is washed with ether, alkalized with an aqueous sodium bicarbonate solution and then extracted with chloroform. The extract is dried and evaporated to remove solvent. The residue is converted to its fumarate and recrystallized from ethanol. 0.04 g of (−)-cis-2-(4-methoxyphenyl)-3-acetoxy-5-(2-aminoethyl)-8-chloro-2,3-dihydro-1,5-benzothiazepin-4(5H)-one.fumarate.⅔ H$_2$O is obtained.

M.p. 117°–120° C. (decomp.)
$[\alpha]_D^{20}$ −66.50° (C=0.40, methanol)

EXAMPLE 15

(1) 1.01 g of 2-tert.-butoxycarbonylthio-4,6-dimethylpyrimidine are added under ice-cooling to a solution of 1.59 g of (−)-cis-2-(4-methoxyphenyl)-3-hydroxy-5-[2-(N-methylamino)-ethyl]-8-chloro-2,3-dihydro-1,5-benzothiazepin-4(5H)-one in 10 ml of dioxane, and the mixture is stirred at room temperature for 2 hours. Then, the mixture is diluted with water, and the aqueous mixture is extracted with a mixture of chloroform and ethyl acetate (1:1). The extract is washed with 10% hydrochloric acid and water, dried and then evaporated to remove solvent. The residue is purified by silica gel chromatography, whereby 1.05 g of (−)-cis-2-(4-methoxyphenyl)-3-hydroxy-5-[2-(N-tert.-butoxycarbonyl-N-methylamino)ethyl]-8-chloro-2,3-dihydro-1,5-benzothiazepin-4(5H)-one are obtained as an oil.

(2) A mixture of 1.67 g of (−)-cis-2-(4-methoxyphenyl)-3-hydroxy-5-[2-(N-tert.-butoxycarbonyl-N-methylamino)ethyl]-8-chloro-2,3-dihydro-1,5-benzothiazepin-4(5H)-one, 15 ml of acetic anhydride and 0.5 ml of pyridine is stirred at 110° C. for 4 hours. Then, the mixture is evaporated under reduced pressure to remove solvent. Benzene is added to the residue, and the mixture is evaporated under reduced pressure to remove solvent. 1.81 g of (−)-cis-2-(4-methoxylphenyl)-3-acetoxy-5-[2-(N-tert.-butoxycarbonyl-N-methylamino)ethyl]-8-chloro-2,3-dihydro-1,5-benzothiazepin-4(5H)-one are obtained as an oil.

IR $\nu_{max}^{CHCl_3}$ (cm$^{-1}$): 1740, 1680
NMR (CDCl$_3$) ppm: 1.41 (9H, s, —C(CH$_3$)$_3$), 1.89 (3H, s, COCH$_3$), 2.93 (3H, s, NCH$_3$), 3.81 (3H, s, OCH$_3$)

(3) 1.5 ml of 25% hydrogen bromide-acetic acid are added under ice-cooling to a solution of 0.65 g of (−)-cis-2-(4-methoxyphenyl)-3-acetoxy-5-[2-(N-tert.-butoxycarbonyl-N-methylamino)ethyl]-8-chloro-2,3-dihydro-1,5-benzothiazepin-4(5H)-one in 7 ml of acetic acid, and the mixture is stirred for 30 minutes. Then, the mixture is diluted with ether, and the precipitates are collected by decantation. Said precipitates are washed with ether and dissolved in water. The solution is neutralized with potassium carbonate and extracted with ethyl acetate. The extract is washed with water, dried and evaporated to remove solvent. The residue is converted to its oxalate and recrystallized from methanol. 0.40 g of (−)-cis-2-(4-methoxylphenyl)-3-acetoxy-5-[2-(N-methylamino)ethyl]-8-chloro-2,3-dihydro-1,5-benzothiazepin-4(5H)-one.oxalate is obtained.

The physico-chemical properties of this product are identical with those of the product obtained in Example 4-(3).

EXAMPLE 16

A mixture of 0.27 g of (−)-cis-2-(4-methoxyphenyl)-3-acetoxy-5-[2-(N-tert.-butoxycarbonyl-N-methylamino)ethyl]-8-chloro-2,3-dihydro-1,5-benzothiazepin-4(5H)-one, 2 ml of formic acid and 0.5 ml of water is stirred at 40° C. for 2 hours. Then, the mixture is diluted with water, and the aqueous mixture is alkalized with potassium carbonate and extracted with ethyl acetate. The extract is washed with water, dried and evaporated to remove solvent. The residue is converted to its oxalate and recrystallized from methanol. 0.21 g of (−)-cis-2-(4-methoxyphenyl)-3-acetoxy-5-[2-(N-methylamino)ethyl]-8-chloro-2,3-dihydro-1,5-benzothiazepin-4(5H)-one.oxalate is obtained.

The physico-chemical properties of this product are identical with those of the product obtained in Example 4-(3).

EXAMPLE 17

A mixture of one g of (±)-cis-2-(4-methoxyphenyl)-3-acetoxy-5-[2-(N-methylamino)ethyl]-8-chloro-2,3-dihydro-1,5-benzothiazepin-4(5H)-one.hydrobromide, 10 ml of an aqueous 5% sodium hydroxide solution and 10 ml of ethanol is stirred at room temperature for 2 hours. Then, water is added to the mixture, and the aqueous mixture is extracted with ethyl acetate. The extract is washed with water, dried and evaporated to remove solvent. The residue is converted to its oxalate and recrystallized from a mixture of dimethylformamide, ethanol and ether. 0.79 g of (±)-cis-2-(4-methoxyphenyl)-3-hydroxy-5-[2-(N-methylamino)ethyl]-8-chloro-2,3-dihydro-1,5-benzothiazepin-4(5H)-one.oxalate is obtained.

M.p. 190°-194° C. (decomp.)

EXAMPLE 18

A mixture of one g of (+)-cis-2-(4-methoxyphenyl)-3-acetoxy-5-[2-(N-methylamino)ethyl]-8-chloro-2,3-dihydro-1,5-benzothiazepin-4(5H)-one.oxalate, 10 ml of an aqueous 5% sodium hydroxide solution and 15 ml of ethanol is treated in the same manner as described in Example 17. The crude product thus obtained is converted to its hyrochloride and recrystallized from a mixture of ethanol and ether. 0.74 g of (+)-cis-2-(4-methoxylphenyl)-3-hydroxy-5-[2-(N-methylamino)ethyl]-8-chloro-2,3-dihydro-1,5-benzothiazepin-4(5H)-one.hydrochloride.½ H$_2$O is obtained.

M.p. 137°-140° C.

$[\alpha]_D^{20}$ +83.4° (C=0.415, methanol)

EXAMPLE 19

110 ml of water is added under cooling to a mixture of 18.7 g of (−)-cis-2-(4-methoxyphenyl)-3-acetoxy-5-[2-(N-methylamino)ethyl-]-8-chloro-2,3-dihydro-1,5-benzothiazepin-4(5H)-one.oxalate, 37.4 g of potassium carbonate and 150 ml of methanol, and the mixture is stirred at room temperature for 2 hours. Then, the mixture is diluted with water, and the aqueous mixture is extracted with chloroform. The extract is washed with water, dried and evaporated to remove solvent. The residue is converted to its hydrochloride and recrystallized from ethanol. 12.13 g of (−)-cis-2-(4-methoxyphenyl)-3-hydroxy-5-[2-(N-methylamino)ethyl]-8-chloro-2,3-dihydro-1,5-benzothiazepin-4(5H)-one.hydrochloride.H$_2$O are obtained.

The physico-chemical properties of this product are identical with those of the product obtained in Example 1-(3).

EXAMPLE 20

A mixture of 0.93 g of (−)-cis-2-(4-methoxyphenyl)-3-acetoxy-5-[2-(N-methylamino)ethyl]-8-chloro-2,3-dihydro-1,5-benzothiazepin-4(5H)-one.oxalate, 8 ml of 22% hydrogen chloride-ethanol and 4 ml of methanol is stirred at room temperature for 3 hours. Then, the mixture is evaporated at room temperature under reduced pressure to remove solvent. Water and chloroform are added to the residue, and the mixture is alkalized with potassium carbonate. The chloroform layer is taken out, washed with water, dried and evaporated to remove solvent. The residue is converted to its fumarate and recrystallized from methanol. 0.56 g of (−)-cis-2-(4-methoxyphenyl)-3-hydroxy-5-[2-(N-methylamino)ethyl]-8-chloro-2,3-dihydro-1,5-benzothiazepin-4(5H)-one.fumarate is obtained.

The physico-properties of the product are identical with those of the product obtained in Example 1-(3).

EXAMPLE 21

1.42 g of (−)-cis-2-(4-methoxyphenyl)-3-acetoxy-5-[2-(N-benzyloxycarbonyl-N-methylamino)ethyl]-8-chloro-2,3-dihydro-1,5-benzothiazepin-4(5H)-one are dissolved in a mixture of 15 ml of conc. HCl and 15 ml of methanol. The solutin is saturated with gaseous hydrogen chloride, and the saturated solution is stirred at room temperature for 19 hours. The mixture is evaporated under reduced pressure at a temperature below 35° C. to remove solvent. The residue is dissolved in 10% HCl. The solution is washed with ether, alkalized with potassium carbonate and then extracted with chloroform. The extract is washed with water, dried and then evaporated to remove solvent. A mixture of ethanol and ethyl acetate is added to the residue, and crystalline precipitates are collected by filtration. 770 mg of (−)-cis-2-(4-methoxyphenyl)-3-hydroxy-5-[2-(N-methylamino)ethyl]-8-chloro-2,3-dihydro-1,5-benzothiazepin-4(5H)-one are obtained.

The physico-chemical properties of this product are identical with those of the product obtained in Example 1-(3).

EXAMPLE 22

A mixture of 1.5 g of (−)-cis-2-(4-methoxyphenyl)-3-acetoxy-5-[2-(N-ethylamino)ethyl]-8-chloro-2,3-dihydro-1,5-benzothiazepin-4(5H)-one.oxalate, 8 ml of an aqueous 10% sodium hydroxide solution, 30 ml of methanol and 8 ml of water is stirred at room temperature for 22 hours. Then, the mixture is diluted with water, and the aqueous mixture is extracted with chloroform. The extract is washed with water, dried and evaporated to remove solvent. The residue is converted to its fumarate and recrystallized from ethanol. 1.23 g of (−)-cis-2-(4-methoxyphenyl)-3-hydroxy-5-[2-(N-ethylamino)ethyl]-8-chloro-2,3-dihydro-1,5-benzothiazepin-4(5H)-one.-fumarate are obtained.

M.p. 138°-142° C. (decomp.)

$[\alpha]_D^{20}$ −81.0° (C=1.0, methanol)

EXAMPLE 23

A mixture of 2 g of (−)-cis-2-(4-methoxyphenyl)-3-acetoxy-5-[2-(N-n-propylamino)ethyl]-8-chloro-2,3-dihydro-1,5-benzothiazepin-4(5H)-one fumarate, 11 ml of an aqueous 10% sodium hydroxide solution, 40 ml of methanol and 11 ml of water is treated in the same manner as described in Example 22. The crude product thus obtained is converted to its fumarate and recrystallized from ethanol. 1.53 g of (−)-cis-2-(4-methoxyphenyl)-3-hydroxy-5-[2-(N-n-propylamino)ethyl]-8-chloro-2,3-dihydro-1,5-benzothiazepin-4(5H)-one.-fumarate are obtained.

M.p. 126°-128° C. (decomp.)

$[\alpha]_D^{20}$ −81.2° (C=1.0, methanol)

EXAMPLE 24

A solution of 1.5 g of (−)-cis-2-(4-methoxyphenyl)-3-hydroxy-5-[2-(N-methylamino)ethyl]-8-chloro-2,3-dihydro-1,5-benzothiazepin-4(5H)-one in 50 ml of methylene chloride is added dropwise to a solution of 4.77 g of boron tribromide in 50 ml of methylene chloride at −50° C. during 30 minutes, and the mixture is stirred at the same temperature for 30 minutes. Then, the mixture is evaporated below 30° C. under reduced pressure to remove solvent. Ice-water and an aqueous sodium bicarbonate solution are added to the residue. The precipitates are collected by decantation. Said precipitates are dissolved in acetone, and insoluble materials are removed by filtration. The filtrate is evaporated under reduced pressure to remove solvent. The residue is converted to its 2-(4-hydroxybenzoyl)benzoic acid salt and then recrystallized from a mixture of ethanol and ether. 0.80 g of (−)-cis-2-(4-hydroxyphenyl)-3-hydroxy-5-[2-(N-methylamino)ethyl]-8-chloro-2,3- dihydro-1,5-benzothiazepin-4(5H)-one. 2-(4-hydroxybenzoyl)benzoic acid salt.3/2 H 0 is obtained.

M.p. 124°–128° C.

$[\alpha]_D^{20}$ −197.48° (C=0.556, methanol)

EXAMPLE 25

0.28 g of sodium hydride (63% oil dispersion) is added to a solution of 1.05 g of (−)-cis-2-(4-methoxyphenyl)-3-hydroxy-5-[2-(N-tert.butoxycarbonyl-N-methylamino)ethyl]-8-chloro-2,3-dihydro-1,5-benzothiazepin-4(5H)-one in a mixture of 10 ml of benzene and one ml of dimethylformamide. The mixture is stirred at room temperature for 30 minutes. Then, 0.92 g of benzyl bromide is added to the mixture, and said mixture is stirred at room temperature for 20 hours. The mixture is diluted with water, and the aqueous mixture is extracted with benzene. The extract is washed with water, dried and evaporated to remove solvent. Then, 7 ml of formic acid and one ml of water are added to the residue (oil: 1.36 g) thus obtained, and the mixture is stirred at 40° C. for 1.5 hours. The mixture is evaporated under reduced pressure to remove solvent. The residue is dissolved in 10% hydrochloric acid, and the solution is washed with ether. The aqueous layer is alkalized with ammonia and extracted with chloroform. The extract is washed with water, dried and evaporated to remove solvent. The residue is converted to its hydrochloride and recrystallized from ethanol. 0.83 g of (+)-cis-2-(4-methoxyphenyl)-3-benzyloxy-5-[2-(N-methylamino)ethyl]-8-chloro-2,3-dihydro-1,5-benzothiazepin-4(5H)-one.hydrochloride is obtained.

M.p. 171°–174° C.

$[\alpha]_D^{20}$ +22.5° (C=0.364, methanol)

EXAMPLE 26

(1) A mixture of 1.40 g of the optical isomer of cis-2-(4-methoxyphenyl)-3-hydroxy-9-chloro-2,3-dihydro-1,5-benzothiazepin-4(5H)-one (Lactam B obtained in preparation 5), 970 mg of 2-(N-benzyl-N-methylamino)ethyl chloride.hydrochloride, 2.0 g of powdered potassium carbonate and 23 ml of acetone is refluxed for 20 hours. Inorganic materials are filtered off and washed with hot acetone. The filtrate and the washings are combined and evaporated under reduced pressure to remove solvent. The residue is purified by silica gel column chromatography (solvent, benzene:ethyl acetate =4:1), whereby 1.67 g of the optical ismoer of cis-2-(4-methoxyphenyl)-3-hydroxy-5-[2-(N-benzyl-N-methylamino)ethyl]-9-chloro-2,3-dihydro-1,5-benzothiazepin-4(5H)-one are obtained as an oil.

(2) A mixture of 2.06 g of the optical isomer of cis-2-(4-methoxyphenyl)-3-hydroxy-5-[2-(N-benzyl-N-methylamino)ethyl-]9-chloro-2,3-dihydro-1,5-benzothiazepin-4(5H)-one obtained in paragraph (1), 20 ml of acetic anhydride and 20 drops of pyridine is heated on a water bath for 2.5 hours, and the mixture is evaporated to remove solvent. Benzene is added to the residue, and the mixture is evaporated to remove solvent (This procedure is repeated 3 times), whereby the optical isomer of cis-2-(4-methoxyphenyl)-3-acetoxy-5-[2-(N-benzyl-N-methylamino)ethyl]-9-chloro-2,3-dihydro-1,5-benzothiazepin-4(5H)-one is obtained as an oil. The product thus obtained is dissolved in 25 ml of benzene, and 1.84 g of benzyloxycarbonyl chloride are added thereto. The mixture is refluxed for 5 hours, and evaporated under reduced pressure to remove solvent. 2.53 g of the optical isomer of cis-2-(4-methoxyphenyl)-3-acetoxy-5-[2-(N-benzyloxycarbonyl-N-methylamino)ethyl]-9-chloro-2,3-dihydro-1,5-benzothiazepin-4(5H)-one are obtained as an oil.

(3) 2.53 g of the optical ismoer of cis-2-(4-methoxyphenyl)-3-acetoxy-5-[2-(N-benzyloxycarbonyl-N-methylamino)ethyl]-9-chloro-2,3-dihydro-1,5-benzothiazepin-4(5H)-one obtained in paragraph (2) are dissolved in 6.5 ml of benzene, and 3.75 ml of 25% HBr-acetic acid are added thereto under ice-cooling. The mixture is stirred at the same temperature for 4 hours, and then evaporated under reduced pressure at room temperature to remove solvent. 200 ml of ether are added to the residue, and an oily substance is collected and washed with ether. The oily substance is dissolved in water, and the aqueous solution is alkalized with aqueous ammonia and then extracted with chloroform. The extract is washed with water, dried and then evaporated to remove solvent. The residue is converted to its hydrochloride and recrystallized from ethanol-ether. 1.24 g of (−)-cis-2-(4-methoxyphenyl)-3-acetoxy-5-[2-(N-methylamino)ethyl]-9-chloro-2,3-dihydro-1,5-benzothiazepin-4(5H)-one.hydrochloride.½ H₂O are obtained.

M.p. 152°–154° C.

$[\alpha]_D^{27}$ −0.85° (C=0.352, methanol)

EXAMPLE 27

735 mg of (−)-cis-2-(4-methoxyphenyl)-3-acetoxy-5-[2-(N-methylamino)ethyl]-9-chloro-2,3-dihydro-1,5-benzothiazepin-4(5H)-one.hydrochloride are dissolved in 15 ml of 25% HCl-ethanol, and the solution is stirred at room temperature for 3 hours. The mixture is evaporated under reduced pressure to remove solvent. The residue is washed with ether and recrystallized from methanol. 622 mg of (+)-cis-2-(4-methoxyphenyl)-3-hydroxy-5-[2-(N-methylamino)ethyl]-9-chloro-2,3-dihydro-1,5-benzothiazepin-4(5H)-one.hydrochloride are obtained.

M.p. 218°–220° C. (decomp.)

$[\alpha]_D^{20}$ +1.96° (C=0.457, methanol)

PREPARATION OF STARTING COMPOUNDS

Preparation 1

(1) 19.75 g of 5-chloro-2-nitro-thiophenol and 27.6 g of methyl trans-3-(4-methoxyphenyl)glycidate are suspended in 200 ml of toluene, and 500 mg of zinc acetate dihydrate are added thereto. The mixture is stirred at room temperature for 3 hours. The mixture is evaporated under reduced pressure to remove solvent. Isopropyl ether is added to the residue, and crystalline precipitates are collected therefrom. The crystals are washed with water and isopropyl ether and then recrystallized from a mixture of benzene and isopropyl ether. 27.66 g of methyl (±)-threo-3-(5-chloro-2-nitrophenylthio)-2-hydroxy-3-(4-methoxyphenyl)propionate are obtained as needles.

M.p. 141°–143° C.

(2-a) A mixture of 22.0 g of methyl (±)-threo-3-(5-chloro-2-nitrophenylthio)-2-hydroxy-3-(4-methoxyphenyl)propionate, 120 ml of 10% sodium hydroxide and 400 ml of methanol is stirred at room temperature for 5 hours. The reaction mixture is acidified with conc. hydrochloric acid, and crystalline precipitates are collected by filtration. The crystals are washed with water, dried and then recrystallized phenylthio)-2-hydroxy-3-(4-methoxyphenyl)propionic acid are obtained as plates.

M.p. 179°–182° C.

(2-b) 8.04 g of (±)-threo-3-(5-chloro-2-nitrophenylthio-2-hydroxy-3-(4-methoxyphenyl)propionic acid are dissolved in 110 ml of methanol, and 3.85 g of L-lysine.hydrochloride are added thereto. 21 ml of a solution of 1N potassium hydroxidemethanol are added to the mixture under ice-cooling, and the mixture is allowed to stand at room temperature. Crystalline precipitates are collected by filtration (the mother liquor is hereinafter referred to as "mother liquor (I)"). The crystals (10.56 g) are recrystallized three times repeatedly from a mixture of dimethylformamide and water (1:1) (the mother liquors are hereinafter referred to as "mother liquor (II)"). 4.29 g of (+)-threo-3-(5-chloro-2-nitrophenylthio)-2-hydroxy-3-(4-methoxyphenyl)propionic acid.L-lysine salt are obtained.

M.p. 244°-246° C. (decomp.)

The product (4.29 g) obtained above is suspended in water, and the suspension is acidified with diluted hydrochloric acid and then extracted with chloroform. The extract is washed with water, dried and then evaporated under reduced pressure to remove solvent. The residue is recrystallized from isopropanol. 3.36 g of (+)-threo-3-(5-chloro-2-nitrophenylthio)-2-hydroxy-3-(4-methoxyphenyl)propionic acid.C₃H₇OH are obtained.

M.p. 93°-97° C.

$[α]_D^{20}$ +138.7° (C=0.623, chloroform)

The mother liquors (I) and (II) obtained above are combined, and concentrated under reduced pressure. Crystalline precipitates are collected by filtration and recrystallized from a mixture of ethanol and water (1:1). 3.61 g of (−)-threo-3-(5-chloro-2-nitrophenylthio)-2-hydroxy-3-(4-methoxyphenyl)propionic acid.L-lysine salt are obtained. The salt (3.61 g) thus obtained is converted into its free acid by using diluted hydrochloric acid and then recrystallized from isopropanol. 2.80 g of (−)-threo-3-(5-chloro-2-nitro-phenylthio)-2-hydroxy-3-(4-methoxyphenyl)propionic acid.C₃H₇OH are obtained.

M.p. 92°-97° C.

$[α]_D^{20}$ −120.2° (C=0.323, chloroform)

(3-a) 350 mg of (±)-threo-3-(5-chloro-2-nitrophenylthio)-2-hydroxy-3-(4-methoxyphenyl)propionic acid are dissolved in a mixture of 5 ml of ethanol and 5 ml of acetic acid, and 40 mg of 10% palladium-charcoal are added thereto. The mixture is shaken at room temperature in hydrogen gas atmosphere for 6 hours under an atmospheric pressure. After the reaction is completed, insoluble materials are filtered off. The filtrate is evaporated under reduced pressure to remove solvent, and the residue is recrystallized from a mixture of dimethylformamide and ethanol. 269 mg of (±)-threo-3-(5-chloro-2-aminophenylthio)-2-hydroxy-3-(4-methoxyphenyl)propionic acid are obtained.

M.p. 189°-191° C. (decomp.)

(3-b) 362 mg of (+)-threo-3-(5-chloro-2-nitrophenylthio)-2-hydroxy-3-(4-methoxyphenyl)propionic acid are treated in the same manner as described in Paragraph (3-a), and the crude product is recrystallized from methanol. 301 mg of (+)-threo-3-(5-chloro-2-aminophenylthio)-2-hydroxy-3-(4-methoxyphenyl)propionic acid are obtained.

M.p. 173°-175° C.

$[α]_D^{20}$ +325.0° (C=0.470, methanol)

(3-c) 350 mg of (−)-threo-3-(5-chloro-2-nitrophenylthio)-2-hydroxy-3-(4-methoxyphenyl)propionic acid are treated in the same manner as described in Paragraph (3-a), and the crude product is recrystallized from methanol. 260 mg of (−)-threo-3-(5-chloro-2-aminophenylthio)-2-hydroxy-3-(4-methoxyphenyl)propionic acid are obtained.

M.p. 171°-173° C.

$[α]_D^{20}$ −330.1° (C=0.357, methanol)

(4-a) A mixture of 2 g of (±)-threo-2-hydroxy-3-(2-amino-5-chlorophenylthio)-3-(4-methoxyphenyl)propionic acid and 150 ml of xylene is refluxed for 25 hours while removing the resulting water by a dehydration apparatus. After cooling, the precipitated crystals are collected by filtration and recrystallized from dimethylformamide. 1.6 g of (±)-cis-2-(4-methoxyphenyl)-3-hydroxy-8-chloro-2,3-dihydro-1,5-benzo-thiazepin-4(5H)-one are thereby obtained.

M.p. 230°-232° C.

(4-b) A mixture of 10 g of (+)-threo-2-hydroxy-3-(2-amino-5-chlorophenylthio)-3-(4-methoxyphenyl)propionic acid and 600 ml of xylene is refluxed for 20 hours. After cooling, the precipitated crystals are collected by filtration. 6.9 g of (+)-cis-2-(4-methoxyphenyl)-3-hydroxy-8-chloro-2,3-dihydro-1,5-benzothiazepin-4(5H)-one are thereby obtained.

M.p. 236°-239° C. (decomp.)

$[α]_D^{20}$ +92.1° (C=1.02, dimethylformamide)

(4-c) A mixture of 9 g of (−)-threo-2-hydroxy-3-(2-amino-5-chlorophenylthio)-3-(4-methoxyphenyl)propionic acid and 500 ml of xylene is treated in the same manner as described in paragraph (4-b). 6.5 g of (−)-cis-2-(4-methoxyphenyl)-3-hydroxy-8-chloro-2,3-dihydro-1,5-benzothiazepin-4(5H)-one are thereby obtained.

M.p. 235°-237° C. (decomp.) $[α]_D^{20}$ −92.0° (C=1.06, dimethylformamide)

Preparation 2

3.36 g of (−)-cis-2-(4-methoxyphenyl)-3-hydroxy-8-chloro-2,3-dihydro-1,5-benzothiazepin-4(5H)-one are dissolved in 10 ml of pyridine, and 0.87 g of acetyl chloride is added dropwise thereto under ice-cooling. The mixture is stirred at room temperature for one hour. Then, the mixture is diluted by addition of chloroform. The diluted mixture is washed with 10% hydrochloric acid and water, and then evaporated under reduced pressure to remove solvent. The residue is recrystallized from a mixture of ether and n-hexane, whereby 3.37 g of (−)-cis-2-(4-methoxyphenyl)-3-acetoxy-8-chloro-2,3-dihydro-1,5-benzothiazepin-4(5H)-one is obtained as needles.

M.p. 139°-142.5° C.

$[α]_D^{20}$ −58.1° (C=1.0, methanol)

Preparation 3

(1) A mixture of 40.58 g of 6-chloro-2-nitrothiophenol, 60.15 g of methyl trans-3-(4-methoxyphenyl)-glycidate, 1 g of zinc acetate.dihydrate and 410 ml of toluene is stirred at room temperature for 3 hours in argon atmosphere. After the reaction is completed, the reaction mixture is evaporated under reduced pressure to remove toluene. Isopropyl ether is added to the residue and the precipitated crystals are collected by filtration. The crystals are recrystallized from a mixture of ethyl acetate and hexane (the filtrate is hereinafter referred to as "mother liquor I"). 62.37 g of methyl threo-2-hydroxy-3-(6-chloro-2-nitrophenylthio)-3-(4-methoxyphenyl)propionate are obtained.

M.p. 110°-111.5° C.

The mother liquor I is subjected to silica gel chromatography (Solvent: benzene-ethyl acetate (20:1)), whereby 2.93 g of methyl threo-2-hydroxy-3-(6-chloro- 2-nitrophenylthio)-3-(4-methoxyphenyl)propionate are further obtained.

M.p. 109.5°–111° C.

(2) A mixture of 62 g of methyl threo-2-hydroxy-3-(6-chloro-2-nitrophenylthio)-3-(4-methoxyphenyl)propionate, 7 g of 10% palladium-charcoal, 500 ml of acetic acid and 500 ml of ethanol is shaken at room temperature in hydrogen gas atmosphere for 11 hours under an atmospheric pressure. After the reaction is completed, insoluble materials are removed by filtration. The filtrate is evaporated under reduced pressure to remove solvent and the residue is recrystallized from a mixture of ethyl acetate and hexane. 51.74 g of methyl threo-2-hydroxy-3-(2-amino-6-chlorophenylthio)-3-(4-methoxyphenyl)propionate are obtained.

M.p. 114°–116° C.

(3) 84 mg of sodium hydride (60% oil dispersion) are added to 2 ml of dimethylsulfoxide, and the mixture is stirred at 70° C. for 40 minutes in argon atmosphere. After cooling the mixture, a solution of 0.368 g of methyl threo-2-hydroxy-3-(2-amino-6-chlorophenylthio)-3-(4-methoxyphenyl)propionate in 1 ml of dimethylsulfoxide is added thereto, and the mixture is stirred at room temperature for 40 minutes. Then, the reaction mixture is poured into a mixture of ice and acetic acid and the precipitated crystals are collected by filtration. Said crystals are washed with water, dried and recrystallized from a mixture of chloroform and ethanol. 0.163 g of (±)-cis-2-(4-methoxyphenyl)-3-hydroxy-9-chloro-2,3-dihydro-1,5-benzothiazepin-4(5H)-one is obtained.

M.p. 249°–252° C. (decomp.)

Preparation 4

(1) A mixture of 18.39 g of methyl threo-2-hydroxy-3-(2-amino-6-chlorophenylthio)-3-(4-methoxyphenyl)-propionate, 90 ml of 10% sodium hydroxide, 200 ml of methanol and 90 ml of water is stirred at room temperature for 4 hours. After the reaction is completed, the reaction mixture is adjusted to a pH of about 2 by adding 10% hydrochloric acid under ice-cooling. The mixture is stirred at room temperature overnight. The precipitated crystals are collected by filtration, washed with water and dried. 16.77 g of threo-2-hydroxy-3-(2-amino-6-chlorophenylthio)-3-(4-methoxyphenyl)propionic acid hemihydrate are obtained.

M.p. 108°–110° C. (recrystallized from a mixture of ethanol and water)

(2) A mixture of 15.77 g of threo-2-hydroxy-3-(2-amino-6-chlorophenylthio)-3-(4-methoxyphenyl)propionic acid.hemihydrate and 630 ml of xylene is refluxed for 18 hours while removing the resulting water by a dehydration apparatus. After cooling the reaction mixture, the precipitated crystals are collected by filtration. 10.44 g of (±)-cis-2-(4-methoxyphenyl)-3-hydroxy-9-chloro-2,3-dihydro-1,5-benzothiazepin-4(5H)-one are obtained.

M.p. 249°–251° C. (decomp.)

When the product is recrystallized from a mixture of dimethylformamide and isopropyl ether, said product shows m.p. 247°–250° C. (decomp.)

Preparation 5

(1) A mixture of 22.39 g of (±)-cis-2-(4-methoxyphenyl)-3-hydroxy-9-chloro-2,3-dihydro-1,5-benzothiazepin-4(5H)-one and 60 ml of pyridine is cooled with ice-water, and 28.4 g of (S)-1-(2-naphthylsulfonyl)-pyrrolidine-2-carbonyl chloride prepared from (S)-1-(2-naphthylsulfonyl)pyrrolidine-2-carboxylic acid and oxalyl chloride in anhydrous benzene) are added thereto. The mixture is stirred at room temperature for 18 hours. After the reaction is completed, water and a mixture of ethyl acetate and chloroform (1:1) are added to the mixture. The organic layer is collected therefrom and washed with 10% hydrochloric acid, water, an aqueous 5% sodium bicarbonate solution and water, successively. The solution is dried and then evaporated. The residue is chromatographed on silica gel (Solvent: benzene-ethyl acetate (9:1)), whereby 18.22 g of the product A (oil, $[\alpha]_D^{20}$ −113.2° (C=0.326, chloroform)) and 17.01 g of the product B (crystalline product, M.p. 106°–123° C., $[\alpha]_D^{20}$ +22.8° (C=0.324, chloroform)) are obtained.

(2-a) A mixture of 17.46 g of the product A obtained in paragraph (1), 41 g of potassium carbonate, 100 ml of water and 200 ml of methanol is stirred at room temperature for 19 hours. After the reaction is completed, the precipitated cystals (needles) are collected by filtration and recrystallized from aqueous methanol. 7.85 g of optical isomer of cis-2-(4-methoxyphenyl)-3-hydroxy-9-chloro-2,3-dihydro-1,5-benzothiazepin-4(5H)-one (this product is referred to as "lactam A") are obtained. Yield: 83.4%

M.p. 188°–189° C.

(2-b) A mixture of 12.75 g of the product B obtained in paragraph (1), 30 g of potassium carbonate, 75 ml of water and 150 ml of methanol is stirred at room temperature for 20 hours. After the reaction is completed, the precipitated crystals (needles) are collected by filtration and recrystallized from aqueous methanol. 6.01 g of optical isomer of cis-2-(4-methoxyphenyl)-3-hydroxy-9-chloro-2,3-dihydro-1,5-benzothiazepin-4(5H)-one (this product is referred to as "lactam B") are obtained. Yield: 91.3%

M.p. 188°–189° C.

Preparation 6

A mixture of 2.27 g of the product B obtained in Preparation 5-(1), 40 ml of an aqueous 5% sodium hydroxide solution and 40 ml of methanol is stirred at room temperature for 18 hours. After the reaction is completed, the mixture is diluted with water and then extracted with chloroform. The extract is washed with water, dried and evaporated to remove solvent. The residue is recrystallized from aqueous methanol, whereby 287 mg of optical isomer of cis-2-(4-methoxyphenyl)-3-hydroxy-9-chloro-2,3-dihydro-1,5-benzothiazepin-4(5H)-one (lactam B) are obtained.

On the other hand, the aqueous layer is adjusted to pH 3–4 with 10% hydrochloric acid and then extracted with chloroform. The extract is washed with water, dried and evaporated to remove solvent. The residue (oil, 1.7 g ) is dissolved in benzene-ether, and then extracted with conc.hydrochloric acid. The hydrochloric acid layer is adjusted to pH 4 with potassium carbonate and then extracted with chloroform. The extract is washed with water, dried and evaporated to remove solvent. 640 mg of (−)-threo-2-hydroxy-3-(2-amino-6-chlorophenylthio)-3-(4-methoxyphenyl)propionic acid are obtained as an oil.

$[\alpha]_D^{20}$ −158° (C=0.520, chloroform)

Preparation 7

600 mg of (−)-threo-2-hydroxy-3-(2-amino-6-chlorophenylthio)-3-(4-methoxyphenyl)propionic acid are dissolved in a mixture of 2 ml of dimethylformamide and 5 ml of dichloromethane. 150 mg of 1-hydroxybenzotriazole and 550 mg of dicyclohexylcarbodiimide are added to the solution. Then, the precipitated dicyclohexylurea (270 mg) is removed by filtration, and the filtrate is evaporated under reduced pressure to remove solvent. The residue is dissolved in ethyl acetate, and the solution is washed with an aqueous 5% sodium bicarbonate solution and water, successively. The washed solution is dried and evaporated to remove ethyl acetate. The residue is recrystallized from aqueous methanol. 414 mg of optical isomer of cis-2-(4-methoxyphenyl)-3-hydroxy-9-chloro-2,3-dihydro-1,5-benzothiazepin-4(5H)-one (lactam B) are obtained. Yield: 72.6%

M.p. 188°–189° C.

What we claim is:

1. A 1,5-benzothiazepine of the formula:

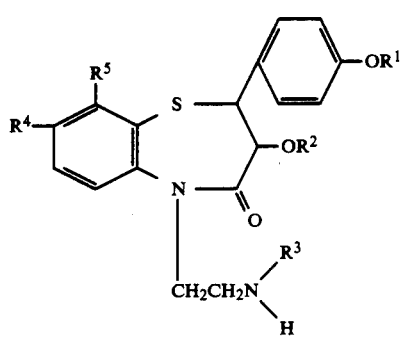

(I)

wherein $R^1$ is hydrogen or lower alkyl, $R^2$ is hydrogen, lower alkanoyl or benzyl, $R^3$ is hydrogen or lower alkyl and either one of $R^4$ and $R^5$ is hydrogen and the other is chlorine, or a pharmaceutically acceptable acid addition salt thereof.

2. A compound according to claim 1, in which $R^1$ is lower alkyl, $R^2$ is hydrogen or lower alkanoyl and $R^3$ is lower alkyl.

3. A compound according to claim 2, in which $R^1$ is methyl, $R^2$ is hydrogen, acetyl, propionyl or butyryl, and $R^3$ is methyl, ethyl or propyl.

4. A compound according to claim 3, in which $R^2$ is hydrogen or acetyl, and $R^3$ is methyl.

5. A compound according to claim 4, in which $R^4$ is chlorine and $R^5$ is hydrogen.

6. A compound according to claim 4, in which $R^4$ is hydrogen and $R^5$ is chlorine.

7. A cis isomer of a compound claimed in claim 1.
8. A cis isomer of a compound claimed in claim 2.
9. A cis isomer of a compound claimed in claim 3.
10. A cis isomer of a compound claimed in claim 4.
11. A cis isomer of a compound claimed in claim 5.
12. A cis isomer of a compound claimed in claim 6.
13. A (−)-cis isomer of a compound claimed in claim 5.

14. The compound according to claim 5, which is (−)-cis-2-(4-methoxyphenyl)-3-hydroxy-5-[2-(N-methylamino)-ethyl]-8-chloro-2,3-dihydro-1,5-benzothiazepin-4(5H)-one or a pharmaceutically acceptable acid addition salt thereof.

15. The compound according to claim 5, which is (−)-cis-2-(4-methoxyphenyl)-3-acetoxy-5-[2-(N-methylamino)-ethyl]-8-chloro-2,3-dihydro-1,5-benzothiazepin-4(5H)-one or a pharmaceutically acceptable acid addition salt thereof.

16. The compound according to claim 6, which is (+)-cis-2-(4-methoxyphenyl)-3-hydroxy-5-[2-(N-methylamino)-ethyl]-9-chloro-2,3-dihydro-1,5-benzothiazepin-4(5H)-one or a pharmaceutically acceptable acid addition salt thereof.

17. A pharmaceutical composition, possessing platelet aggregation-inhibiting activity which comprises as the essential active ingredient a therapeutically effective amount of a compound as claimed in claim 1 in admixture with a conventional pharmaceutically acceptable carrier or diluent.

18. A pharmaceutical composition according to claim 17, wherein the essential active ingredient is the compound as claimed in claim 2.

19. A pharmaceutical composition according to claim 17, wherein the essential active ingredient is the compound as claimed in claim 4.

20. A method of producing a platelet aggregation-inhibiting effect on a warm-blooded animal comprising administering to said warm-blooded animal an effective amount of the compound claimed in claim 1.

21. A pharmaceutical composition according to claim 17 wherein the essential active ingredient is the compound of claim 14.

22. A pharmaceutical composition according to claim 17 wherein the essential active ingredient is the compound of claim 15.

23. A pharmaceutical composition according to claim 17 wherein the essential active ingredient is the compound of claim 16.

* * * * *